United States Patent
Eliasen et al.

(10) Patent No.: US 6,332,874 B1
(45) Date of Patent: Dec. 25, 2001

(54) COUPLING AND STABILIZATION SYSTEM FOR PROXIMAL END OF CATHETER

(75) Inventors: Kenneth A. Eliasen, Queensbury, NY (US); Kelly B. Powers, North Salt Lake; Daniel T. Schlehuber, Sandy, both of UT (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/143,275

(22) Filed: Aug. 28, 1998

Related U.S. Application Data

(63) Continuation-in-part of application No. 29/091,063, filed on Apr. 20, 1999, now Pat. No. Des. 408,530.

(51) Int. Cl.$^7$ .................................................. A61M 5/32
(52) U.S. Cl. ............................... 604/174; 128/DIG. 6; 128/DIG. 26
(58) Field of Search ................... 604/174, 177, 604/179, 180, 164, 165, 164.01–164.02, 164.04, 164.13–165.01, 165.03; 128/DIG. 6, DIG. 26

(56) References Cited

U.S. PATENT DOCUMENTS

| D. 208,611 | 9/1967 | Smith, Jr. ............................... D83/12 |
| D. 217,702 | 5/1970 | Volk et al. ............................. D83/12 |
| D. 220,555 | 4/1971 | Reiterman .............................. D83/12 |
| D. 223,043 | 2/1972 | Raines .................................. D83/12 |
| D. 224,727 | 9/1972 | Rychlik ................................. D83/12 |
| D. 228,691 | 10/1973 | Stocton ............................... D83/12 A |
| D. 257,885 | 1/1981 | Kulle ................................... D24/52 |
| D. 258,387 | 2/1981 | De Frank .............................. D24/52 |
| D. 314,050 | 1/1991 | Sone ................................... D24/53 |
| D. 326,154 | 5/1992 | Deguchi et al. ...................... D24/112 |

(List continued on next page.)

FOREIGN PATENT DOCUMENTS

| 168289 | 1/1986 | (EP) | ............................... A61M/25/02 |
| 801954 | 10/1997 | (EP) | ............................... A61M/25/00 |
| WO 99/44654 | 9/1999 | (WO) | ............................... A61M/5/00 |

OTHER PUBLICATIONS

Bard Access Systems, "Devices for Small Patients" (Jul. 1992).
GESCO International, Inc., "Thora–Cath: A Silicone Chest Drainage Catheter" (1995).
GESCO International, Inc., "Per–Q–Cath Product Specification" (1995).
Bard Access Systems, "Assessment Advantage$^{SM}$ Cost Reduction and Patient Outcomes Program" (1996).
Bard Access Systems, "Per–Q–Cath™ Catheters: Simplicity in PICC Placement" (1996).

(List continued on next page.)

Primary Examiner—Richard K. Seidel
Assistant Examiner—LoAn H. Thanh
(74) Attorney, Agent, or Firm—TraskBritt

(57) ABSTRACT

A conduit of relatively tough biocompatible material encloses a longitudinally extending fluid flow lumen and has a distal end configured as a catheter coupling hub. The conduit is encircled at the distal end of the catheter coupling hub and a portion of the conduit distal of and adjacent to the catheter coupling hub by a stabilization sleeve made of a contrastingly resilient, soft material suitable for skin contact applications. A pair of stabilization wings extends laterally on opposite sides from the stabilization sleeve at an attachment location separated from the portion of the stabilization sleeve in which the catheter coupling hub is received. As a result, a strain relief region is created. The stabilization sleeve is permanently attached to the conduit at the coupling hub only. The portion of the conduit distal of and adjacent to the catheter coupling hub extends slideably through the remainder of the length of the stabilization sleeve affording axial and bending strain relief to that portion of the conduit.

38 Claims, 9 Drawing Sheets

U.S. PATENT DOCUMENTS

| | | | |
|---|---|---|---|
| D. 328,788 | 8/1992 | Sagae et al. | D24/129 |
| D. 340,111 | 10/1993 | Yoshikawa | D24/112 |
| D. 355,031 | 1/1995 | Yoshikawa | D24/112 |
| D. 358,465 | 5/1995 | Klein et al. | D24/112 |
| D. 376,646 | 12/1996 | Vallelunga | D24/130 |
| D. 381,419 | 7/1997 | Musgrave et al. | D24/112 |
| D. 384,740 | 10/1997 | Musgrave et al. | D24/112 |
| D. 395,501 | 6/1998 | Erskine et al. | D24/112 |
| D. 408,530 | 4/1999 | Eliasen et al. | D24/112 |
| 3,454,006 | 7/1969 | Langdon | 128/214.4 |
| 3,640,275 | 2/1972 | Burke et al. | 128/214 |
| 3,983,203 | 9/1976 | Corbett | 264/150 |
| 4,129,128 * | 12/1978 | McFarlane . | |
| 4,193,399 | 3/1980 | Robinson | 128/214.4 |
| 4,194,504 | 3/1980 | Harms et al. | 128/214.4 |
| 4,300,553 | 11/1981 | Seberg | 128/214.4 |
| 4,316,461 | 2/1982 | Marais et al. | 128/214 R |
| 4,323,065 | 4/1982 | Kling | 128/214 R |
| 4,341,212 | 7/1982 | Medwid | 128/276 |
| 4,362,156 | 12/1982 | Feller, Jr. et al. | 604/165 |
| 4,366,817 | 1/1983 | Thomas | 604/174 |
| 4,388,074 * | 6/1983 | Seberg et al. | 604/165 |
| 4,389,210 | 6/1983 | Genese | 604/177 |
| 4,417,887 | 11/1983 | Koshi | 604/162 |
| 4,445,893 | 5/1984 | Bodicky | 604/165 |
| 4,460,356 | 7/1984 | Moseley | 604/180 |
| 4,482,592 | 11/1984 | Kramer | 428/67 |
| 4,600,402 | 7/1986 | Rosenberg | 604/96 |
| 4,609,370 * | 9/1986 | Morrison | 604/165 |
| 4,650,472 | 3/1987 | Bates | 604/158 |
| 4,710,175 | 12/1987 | Cartmell et al. | 604/177 |
| 4,738,658 | 4/1988 | Magro et al. | 604/53 |
| 4,743,265 | 5/1988 | Whitehouse et al. | 604/161 |
| 4,748,982 | 6/1988 | Horzewski et al. | 128/344 |
| 4,775,367 | 10/1988 | Schmidt | 604/192 |
| 4,781,692 | 11/1988 | Jagger et al. | 604/164 |
| 4,838,269 * | 6/1989 | Robinson et al. . | |
| 4,863,426 | 9/1989 | Ferragamo et al. | 604/93 |
| 4,863,432 * | 9/1989 | Kvalo | 604/177 |
| 5,151,962 * | 9/1992 | Walker et al. . | |
| 5,163,913 * | 11/1992 | Rantanen-Lee et al. | 604/177 |
| 5,167,635 | 12/1992 | Haber et al. | 604/164 |
| 5,167,647 | 12/1992 | Wijkamp et al. | 604/281 |
| 5,234,410 | 8/1993 | Graham et al. | 604/167 |
| 5,234,411 | 8/1993 | Vaillancourt | 604/171 |
| 5,267,971 | 12/1993 | Brimhall | 604/177 |
| 5,304,144 * | 4/1994 | Brimhall . | |
| 5,330,449 | 7/1994 | Prichard et al. | 604/282 |
| 5,358,493 * | 10/1994 | Schweich, Jr. et al. | 604/264 |
| 5,380,301 * | 1/1995 | Prichard et al. | 604/281 |
| 5,405,336 | 4/1995 | Austin et al. | 604/280 |
| 5,423,763 | 6/1995 | Helland et al. | 604/174 |
| 5,489,273 | 2/1996 | Whitney et al. | 604/160 |
| 5,531,701 * | 7/1996 | Luther | 604/165 |
| 5,536,255 | 7/1996 | Moss | 604/161 |
| 5,628,780 | 5/1997 | Helland et al. | 607/126 |
| 5,632,754 | 5/1997 | Farley et al. | 606/159 |
| 5,651,776 * | 7/1997 | Appling et al. | 604/283 |
| 5,674,201 | 10/1997 | Steinman | 604/165 |
| 5,695,506 | 12/1997 | Pike et al. | 606/159 |
| 5,772,643 | 6/1998 | Howell et al. | 604/283 |
| 5,800,410 | 9/1998 | Gawreluk | 604/280 |
| 5,807,342 * | 9/1998 | Musgrave et al. | 604/177 |
| 5,810,780 | 9/1998 | Brimhall et al. | 604/167 |
| 5,814,021 | 9/1998 | Balbierz | 604/174 |
| 5,827,230 | 10/1998 | Bierman | 604/174 |
| 5,941,849 * | 8/1999 | Amos, Jr. et al. | 604/95 |
| 6,011,988 | 1/2000 | Lynch et al. | 600/434 |
| 6,074,379 | 6/2000 | Prichard | 604/524 |

OTHER PUBLICATIONS

Bard Access Systems, "Midline Groshong® & Per–Q–Cath® Catheters:Color Coded for Easy Identification" (Aug. 1996).

Bard Access Systems, "Per–Q–Cath™ PICC and Midline Dressing Change" (1997).

Cook Incorporated, "Peripherally Inserted Central Venous Catheter Sets" (1997).

Winged venipuncture needle set of VIGGO (circa 1989).

Hickman® dual lumen chronic care cardiovascular access hemodialysis catheter of Bard Access Systems (circa 1991).

Flexxicon II® dual lumen acute care cardiovascular access hemodialysis catheter of Vas–Cath Incorporated (circa 1992).

Vaccess™ single lumen acute care cardiovascular access catheter with Y–side port of Vas–Cath Incorporated (circa 1988).

Per–Q–Cath® peripherally inserted central venous catheter of GESCO International, Inc. (circa 1992).

Per–Q–Cath® midline catheter of GESCO International, Inc. (circa 1998).

* cited by examiner

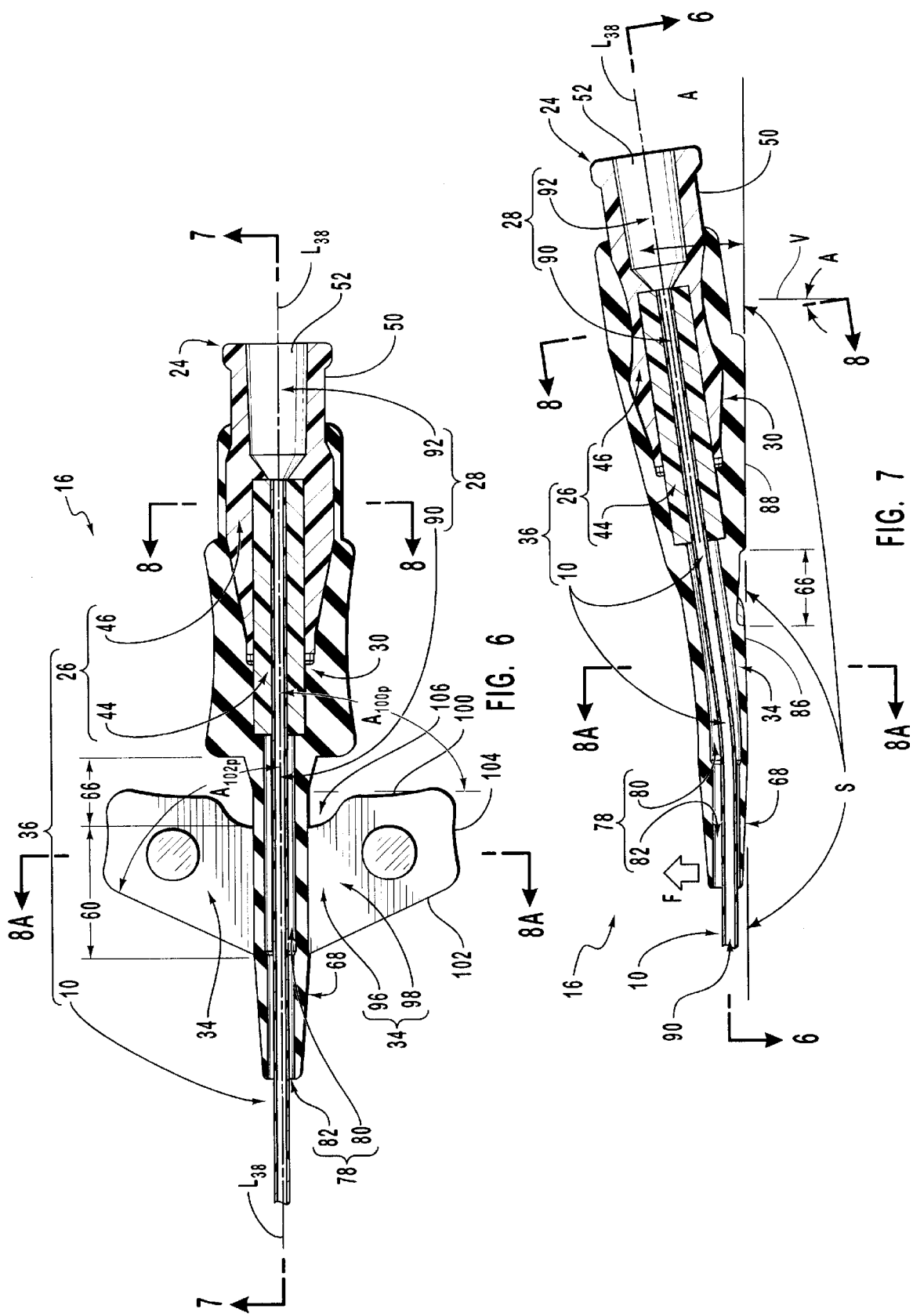

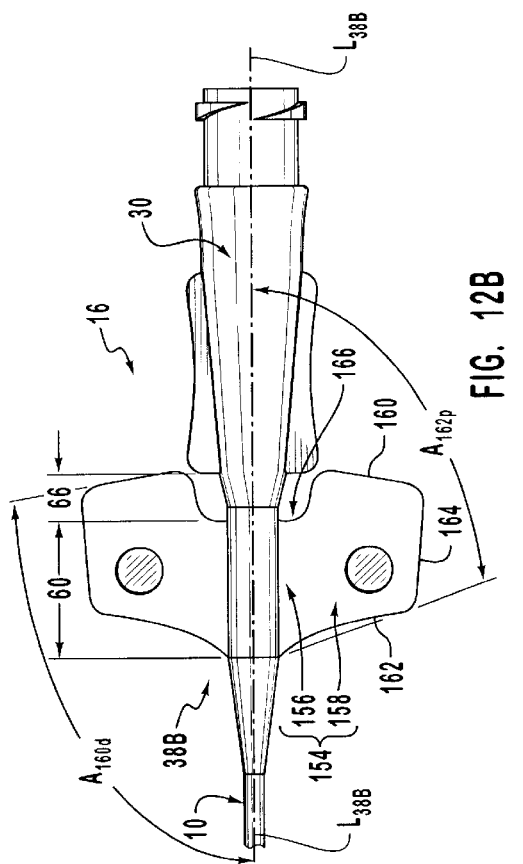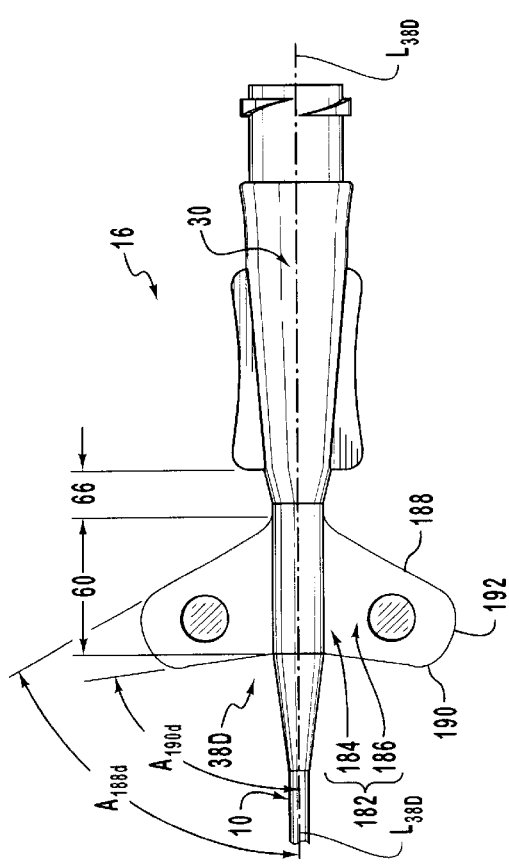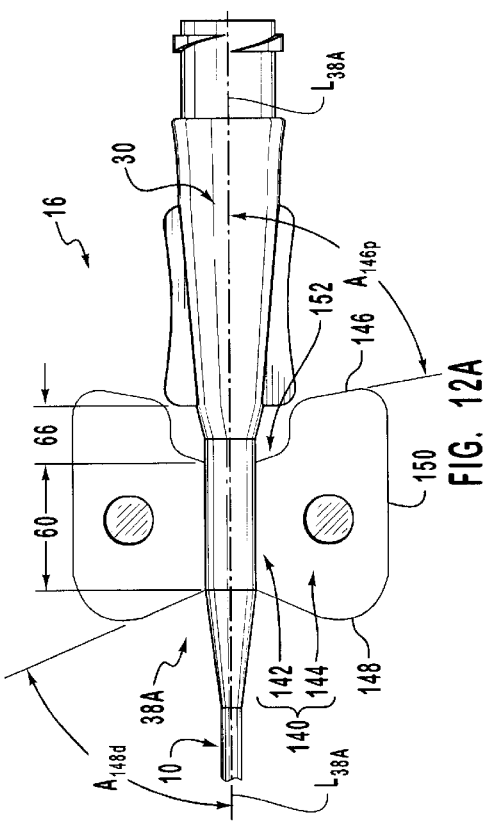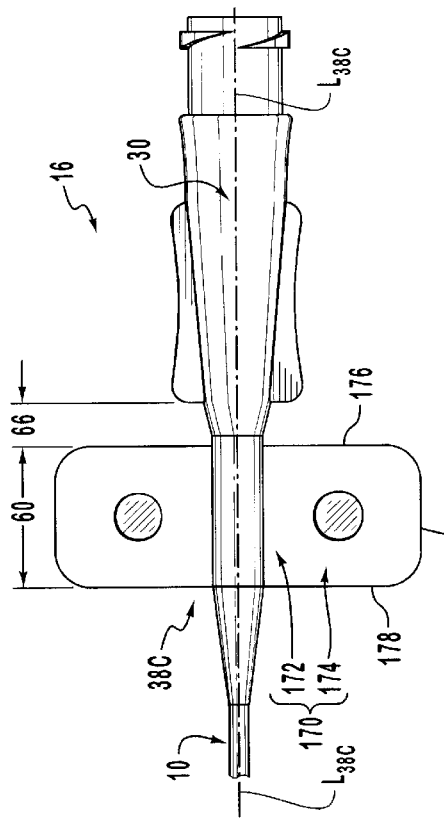

COUPLING AND STABILIZATION SYSTEM FOR PROXIMAL END OF CATHETER

RELATED APPLICATIONS

This is a United States continuation-in-part application of U.S. appl. Ser. No. 29/091063, filed Apr. 20, 1999 now U.S. Pat. No. Des. 408,530 that issued on Apr. 20, 1999, from U.S. Design patent application Ser. No. 91,063 that was filed on Jul. 22, 1998.

BACKGROUND

1. The Field of the Invention

This invention pertains to implantable catheters, and, more particularly, to systems for effecting the stabilization on the skin of a patient of the extracorporeal portion of an implanted vascular access catheter.

2. Background Art

It is now common to use an implanted catheter to repeatedly access the vascular system of a patient and with the catheter perform repeated therapeutic medical activity. Such therapeutic activity could include the intermittent or continuous infusion of medication and fluids, the periodic sampling of blood, or the continuous withdrawal and return of blood for processing outside of the body of the patient. The catheters used in these activities are referred to as vascular access catheters.

Before any therapeutic activity can actually commence, however, the vascular access catheter must be implanted in the body of the patient with the distal tip of the catheter residing at the location in the vascular system at which an intended therapeutic activity is appropriate. Typically, most of the length of an implanted vascular access catheter resides within blood vessels of the vascular system, extending from the distal tip of the catheter to a location in the vascular system at which the catheter, by traversing a puncture or incision formed through a wall of the blood vessel in which the catheter is disposed, enters into the surrounding subcutaneous tissue of the patient. The location at which this occurs is referred to as a venipuncture site. Venipuncture sites are classified on the basis of the position of a venipuncture site in relation to the center of the body of the patient. Central venipuncture sites are those at the superior or inferior vena cava. Midlavicular venipuncture sites are located medial of the shoulder of the patient, but lateral of the subclavian vein. Midline venipuncture sites enter the upper basilic or cephalic veins. The freedom to select among venipuncture sites is most curtailed relative to patients of slight stature, particularly small children and infants.

Proximal of the venipuncture site, the implanted catheter extends through the subcutaneous tissue of the patient to emerge through the skin at a location that is referred to as the skin exit site. Most skin exit sites are chosen as being locations at which the proximal end of the implanted catheter can be easily manipulated by medical personnel. Favored among such locations are the neck, the region about the collar bone, the upper leg, the upper arm, and the forearm.

Occasionally, the skin exit site is somewhat removed from the venipuncture site. Then a significant portion of the length of the implanted catheter must be embedded in the subcutaneous tissue of the patient in a surgically created tunnel that extends from the venipuncture site to the skin exit site. The disposition of a significant portion of the length of an implanted catheter in such a subcutaneous tunnel assists in stabilizing the implanted catheter by resisting sliding movement of the catheter back and forth, internally at the venipuncture site or externally at the skin exit site.

On the other hand, with patients of slight stature and particularly with small children and infants, the skin exit site is frequently located immediately adjacent to the venipuncture site. Under such conditions, the portion of the implanted catheter disposed in subcutaneous tissue is so short as to permit the body of the catheter to slide back and forth across the venipuncture site, as well as in and out of the skin exit site.

The portion of an implanted catheter that resides in a blood vessel of the vascular access system or within subcutaneous tissue is referred to as the implanted portion of that catheter. In all instances, a portion of the proximal end of an implanted catheter must remain outside of the body of the patient. It is this portion of an implanted catheter, from the proximal end thereof to the skin access site, that is referred to as the extracorporeal portion of the implanted catheter.

The extracorporeal portion of an implanted catheter must be capable of being selectively coupled to and uncoupled from the tubing and medical equipment outside the body of the patient that are required for therapeutic activity. Accordingly, the proximal end of virtually all vascular access catheters terminates in a catheter coupling hub that can be secured in fluid communication with such tubing and medical equipment, or can be capped, valved, or clamped closed between periods of actual use.

The repeated manipulation of the extracorporeal portion of an implanted catheter causes wear in the material of the catheter and reduces the reliability of the attachment between the proximal end of the catheter and the catheter coupling hub. In the absence of countermeasures, forces imposed on the extracorporeal portion of an implanted catheter result in motions of the extracorporeal portion of the catheter that cause damage to the catheter. Motion of the extracorporeal portion of an implanted catheter is also communicated to the skin access site, causing various complications depending upon the length of any subcutaneous tunnel in which a portion of the catheter is imbedded. Where such a subcutaneous tunnel is lengthy, motions of the extracorporeal portion of a catheter are relayed directly to the tissue along the subcutaneous tunnel, causing pain and irritation, precluding healing, and leading to infection. These results in turn can necessitate the explanation of the catheter. Where the portion of an implanted catheter extending subcutaneously between the venipuncture site and the skin exit site is short, motions of the extracorporeal portion of the catheter tend to slide the catheter in and out of the vascular system, causing bleeding and likewise leading to infection.

To counteract these undesirable consequences, a variety of measures are undertaken to stabilize the extracorporeal portion of an implanted catheter on the skin of the patient. Tie-down materials, such as bandaging, patches with upstanding anchoring posts, medical adhesive tape, belts, elastic bands, and sutures, are used for this purpose.

To enhance the effectiveness of such tie-down materials, otherwise unnecessary structures are formed on or attached to the catheter coupling hub or the portion of the proximal end of the catheter attached thereto. For example, it is common in the art of catheter implantation to provide one or more flap-like structures that extend laterally from the catheter coupling hub, from the portion of the proximal end of the catheter attached thereto, or from a tubular sleeve that is disposed about either or both of the catheter and the catheter coupling hub. These structures are referred to as stabilization wings.

Even without the assistance of any tie-down materials, a stabilization wing prevents a catheter coupling hub from rolling along the skin of the patient, pivoting about the skin exit site, and twisting the extracorporeal portion of the catheter between the skin exit site and the coupling hub. Sliding motions of a coupling hub on the skin of the patient in directions normal to the length of the catheter are curtailed by the use of tie-down materials applied over or about the coupling hub and against the skin. Tie-down materials also prevent movement of the coupling hub and associated catheter in directions aligned with the length of the catheter, motions that could dislodge the catheter from the skin exit site entirely. Stabilization wings enhance the purchase afforded on the catheter coupling hub by tie-down materials.

A system for coupling an implanted catheter to extracorporeal medical equipment and simultaneously stabilizing the extracorporeal portion of that catheter is complex to design. It is a process that must accommodate a variety of functional needs in an environment involving materials as different as human tissue, bodily fluids, flexible fluid conduits, rigid coupling structures, and various tie-down materials. The extracorporeal portion of an implanted catheter functions as an interface between the environment within the body of the patient at the distal tip of the catheter and extracorporeal medical equipment. At this interface, the patency of tubing, the minimizing of wear, the suppression of exit site infection, the freedom of access by medical personnel, and the inconspicuousness of the extracorporeal portion of the implanted catheter are each desired to be maintained to optimum degrees.

As new classes of materials are developed that are suitable for medical use, the potential of each in relation to existing catheter coupling and stabilization systems is investigated, and the design of such systems evolves accordingly.

Nonetheless, a significant problem in the design of coupling and stabilization systems arises from the contradictory material properties considered desirable among the various components of such systems.

The criteria of suitability for the implanted portion of a catheter that is disposed in the vascular system or the subcutaneous tissue of a patient are dramatically different from the criteria of suitability for the environment outside the body in which the extracorporeal portion of an implanted catheter is disposed and utilized. The implanted portion of a vascular access catheter must be so flexible and soft as to avoid damaging internal tissues and to minimize injury to the cells of the blood. The extracorporeal portion of that same implanted catheter must, by contrast, sustain repeated manipulation and predictable accidental or intentional abuse.

Among the extracorporeal portion of an implantable catheter assembly are components that are hard and entirely inflexible, such as clamps and coupling fixtures that must interact with extracorporeal tubing and medical equipment. In view of the possibility of extended contact by the extracorporeal portion of an implanted catheter with the skin of the patient, contrasting material properties of softness and flexibility suitable for skin contacting applications are also desirable in the extracorporeal interface.

Thus, many desirable material properties are inconsistent with others. As a result, efforts to optimize coupling and stabilization system designs have on occasion used differing classes of materials in various distinct components of the catheter coupling and stabilization system. The tension between the mechanical properties required in the extracorporeal interface for an implanted catheter and the patient comfort properties desirable therein has been resolved only to varying degrees in different systems.

One approach to achieving a marriage of the inconsistent material properties desired in a coupling and stabilization system has been to resort to nonunitary coupling and stabilization systems. Such systems involve some components that embody one set of desired material properties that are assembled in the field by medical personnel with other components that embody a contrasting set of desired material properties. For example, brackets optimizing patient comfort properties are secured to the skin of a patient and used as retainers to stabilize catheter coupling hubs made of tough materials possessed of optimized mechanical properties.

Coupling and stabilization systems configured from components assembled in the field are disadvantaged, however. Individual components can become lost, mismatched components can inadvertently be used together, or important components may never be employed as a result of slipshod practices. Individual components are small and difficult to manipulate, while the maintenance of inventories of a variety of individual interconnecting coupling and stabilization system elements increases institutional overhead.

The selection of structural elements for the extracorporeal interface and the relative positioning of the selected structural elements in a given coupling and stabilization system similarly require design trade-offs that are unlikely to be optimized in any single system.

For example, coupling and stabilization systems that utilize stabilization wings positioned at or adjacent to the catheter coupling hub of the system are effective in precluding movement of the catheter coupling hub. This high level of stability in the catheter coupling hub is obtained, however, at the cost of restricting the ease with which the catheter coupling hub can be manipulated by medical personnel. When stabilization wings in an extracorporeal interface are positioned longitudinally at or close to a catheter coupling hub, the stabilization wings and the catheter coupling hub share relatively similar degrees of freedom. As a consequence, the coupling and uncoupling of extracorporeal tubing and medical devices at the catheter coupling hub are undesirably difficult. Forces imposed on the catheter coupling hub or on the portion of the proximal end of the catheter attached thereto, and motions imparted to either as a result, are communicated directly to the stabilization wings, tending to dislodge the stabilization wings from the skin of the patient. This can be uncomfortable and may lead to tissue irritation at that location. Dislodgment of stabilization wings or a coupling hub from associated tie-down materials or from the skin is likely to lead to catheter damage or catheter explanation.

The positioning of stabilization wings along the proximal end of a catheter distally from the catheter coupling hub produces a different mix of consequences.

Stabilization wings have been longitudinally fixed on the exterior of the extracorporeal portion of a catheter tube at a distance from the catheter coupling hub. When secured to the skin of a patient, the stabilization wings of such systems permit easy access to and use of the catheter coupling hub, because of the flexibility embodied in the material of the catheter between the stabilization wings and the catheter coupling hub. Nonetheless, tortional and axial forces imposed on the catheter coupling hub are still communicated directly to the stabilization wings, as surely as if those stabilization wings were positioned immediately at the catheter coupling hub.

In some coupling and stabilization systems, stabilization wings are attached to the distal end of an elongated sleeve that is in turn secured at the proximal end thereof to the exterior of the catheter coupling hub. The full length of the interior of the sleeve is bonded to the exterior of the catheter tube distal of and adjacent to the coupling hub, producing a composite structure distal of the coupling hub. Such sleeves thicken, and therefore strengthen, the portion of the catheter tube enclosed therein, increasing the durability of the composite structure. Nonetheless, the composite structure tends to exhibit reduced flexibility, impairing intended movements of the catheter coupling hub relative to the stabilization wings. Also, axial forces imposed on the catheter coupling hub are communicated directly to the stabilization wings.

Some of these difficulties may be overcome, but not without foregoing other advantages.

Stabilization wings are, on occasion carried on a sleeve that can be slid along the extracorporeal portion of an implanted catheter and positioned on the skin of the patient at any desired distance from the catheter coupling hub. The securement of such stabilization wings to the skin prevents lateral movement of the portion of the catheter that is between the stabilization wings and the skin exit site. As the sleeve carrying the stabilization wings is not secured in any fixed relation to the catheter or the coupling hub, undesirable longitudinal and rotational movement of the catheter coupling hub relative to the stabilization wings is nonetheless common. Stabilization wings carried on slidable sleeves are susceptible to disposition at improper locations and are thus sensitive to, and in some cases limited in utility by, the skill and talent of specific medical personnel. Slidable sleeves may be overlooked and never used. Some are simply severed from the catheter assembly out of a misplaced desire to simplify the extracorporeal portion of the implanted structure. Longitudinally positionable sleeves carrying stabilization wings are known that completely succumb to this impulse by being manufactured with an axial slit through the sleeve. The sleeve may then be detached at will from the system of which it is supposed to be a component.

It may be realistic in addressing the diverse demands placed on the extracorporeal interface of an implanted catheter to acknowledge that any distinct coupling and stabilization system is advantageous in selected respects and disadvantaged in others.

SUMMARY OF THE INVENTION

Accordingly, one broad objective of the present invention is to facilitate the delivery of medical care by improving the capacity of medical personnel to perform repeated therapeutic medical activity in the vascular system of a patient.

Correspondingly, another objective of the present invention is to simultaneously improve the mechanical reliability and the patient comfort provided by the extracorporeal portion of an implanted vascular catheter.

In this regard, it is an objective of the present invention to provide a catheter coupling and stabilization system that is not sensitive to or limited by the skill and talent of medical personnel, but rather is a failsafe system.

An additional object of the present invention is to optimize tradeoffs in a catheter coupling and stabilization system between the advantages of material toughness and the desirability of ergonomic compatibility.

It is also an object of the present invention to provide such a system from which it is not possible to lose, misplace, or misposition constituent components.

Yet another objective of the present invention is a catheter coupling and stabilization system as described above, that is able to reduce skin irritation and infection at the skin exit site, while yet permitting easy manipulation of the catheter coupling hub of the system by medical personnel.

It is a further object of the present invention to provide a catheter coupling and stabilization system in which forces imposed to a catheter coupling hub and the resulting motions imparted thereto avoid being transmitted directly to structures of the system that are used to secure the extracorporeal portion of the implanted catheter to the skin of a patient.

Another object of the present invention is to reduce the likelihood of bleeding or infection at the skin exit site for an implanted vascular access catheter, thereby to prolong the potential duration of the catheter in an implanted condition.

It is yet another object of the present invention that a catheter coupling system as described above readily communicate to users of the system the size of the catheter with which the system is employed.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, an implantable vascular access catheter is provided that includes a conduit of relatively tough biocompatible material and an elastomeric sleeve suitable for skin contact applications that encircles some part of the extracorporeal portion of the implanted conduit. Typically, the distal end of the conduit is configured as a catheter coupling hub by which to effect mechanical and fluid interactions with extracorporeal medical equipment. A pair of stabilization wings extends laterally from opposite sides of the sleeve at an attachment location that is separated from the catheter coupling hub.

As a result of this spatial separation, and in view of the elastomeric composition of the sleeve, a strain relief region results in the sleeve between the stabilization wings and the location of the catheter coupling hub in the sleeve.

Therefore, according to one aspect of the present invention, a catheter as described above includes resilient means for reducing motion imparted to the skin of the patient by the stabilization wings due to motion imparted to the catheter coupling hub. According to teachings of the present invention, structures performing this function are optimally located between the attachment location on the sleeve for the stabilization wings and the catheter coupling hub that is encircled at least in part by the sleeve.

In accordance with yet another aspect of the present invention, a stabilization sleeve as described above includes an elongated tube having a proximal end, a distal end, and a passageway extending longitudinally between the proximal end and the distal end. The passageway is sized to slideably receive the catheter that is to be used with the stabilization sleeve. A catheter coupling hub receiving socket is included at the proximal end of the tube, and at least the distal end of the catheter coupling hub or the catheter assembly intended to be used with the stabilization sleeve is secured in the receiving socket. The portion of the catheter distal of and adjacent to the catheter coupling hub extends freely through the remainder of the passageway through the stabilization sleeve.

While numerous materials are likely to prove adequate as constituent materials of each respective portion of the coupling and stabilization system, various types of tough polyurethane have been found to be effective for the conduit of the system, while medical grade silicone is the material of choice for the stabilization sleeve.

BRIEF DESCRIPTION OF THE DRAWINGS

In order that the manner in which the above-recited and other advantages and objects of the invention are obtained, a more particular description of the invention briefly described above will be rendered by reference to specific embodiments thereof that are illustrated in the appended drawings. Understanding that these drawings depict only typical embodiments of the invention and are not therefore to be considered limiting of the scope thereof, the invention will be described and explained with additional specificity and detail through the use of the accompanying drawings in which:

FIG. 6 is a plan view in cross section of the assembled state of the coupling and stabilization system shown in FIG. 2 taken along section line 6—6 therein;

FIG. 7 is an elevation view in cross section of the assembled state of the coupling and stabilization system shown in FIG. 2 taken along section line 7—7 therein;

FIG. 12A is a plan view of a second embodiment of a stabilization sleeve of the type illustrated in FIG. 3;

FIG. 12B is a plan view of a third embodiment of a stabilization sleeve of the type illustrated in FIG. 3;

FIG. 12C is a plan view of a fourth embodiment of a stabilization sleeve of the type illustrated in FIG. 3; and FIG. 12D is a plan view of a fifth embodiment of a stabilization sleeve of the type illustrated in FIG. 3.

DESCRIPTION OF THE PREFERRED EMBODIMENT

Figure 1:
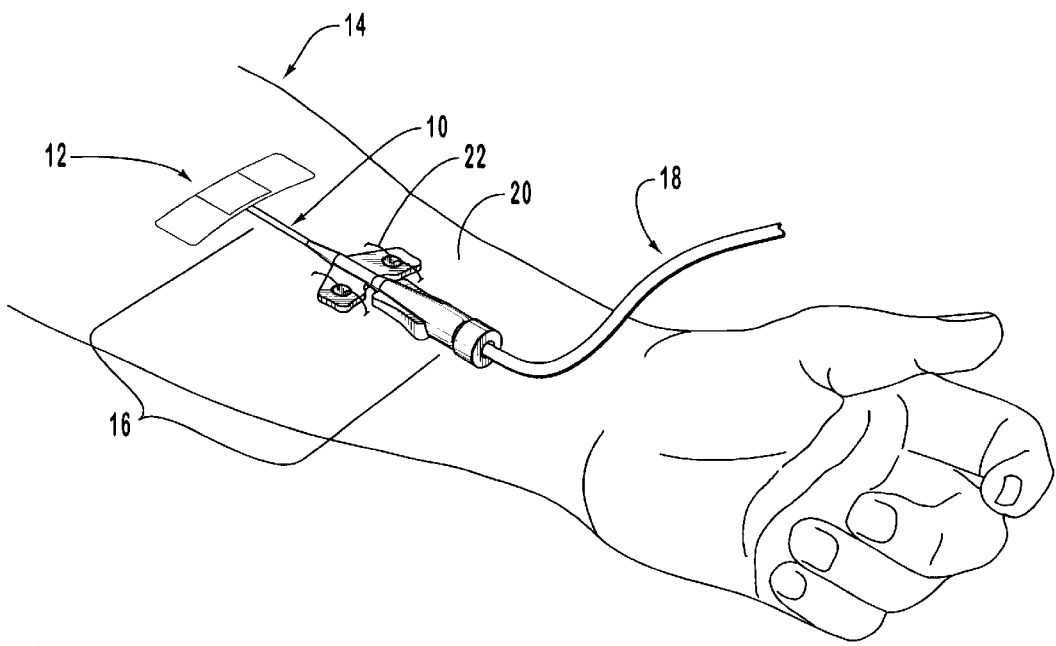
FIG. 1 is a perspective view of the extracorporeal portion of an implanted vascular access catheter having a coupling and stabilization system that incorporates teachings of the present invention and that is connected thereby to extracorporeal medical tubing.

FIG. 1 illustrates in perspective view the extracorporeal portion of a vascular access catheter 10 implanted in the body of a patient at a skin exit site 12 located on the forearm 14. The portion of vascular access catheter 10 illustrated in FIG. 1 utilizes a coupling and stabilization system 16 that incorporates teachings of the present invention and that is connected thereby to extracorporeal medical tubing 18. Coupling and stabilization system 16 is shown by way of example in FIG. 1 as being secured to the skin 20 of forearm 14 by suture ties 22, although coupling and stabilization system 16 is configured for ready stabilization on the skin of a patient using a plurality of other types of tie-down materials, such as bandaging, patches with upstanding anchoring posts, medical adhesive tape, belts, and elastic bands.

Figure 2:
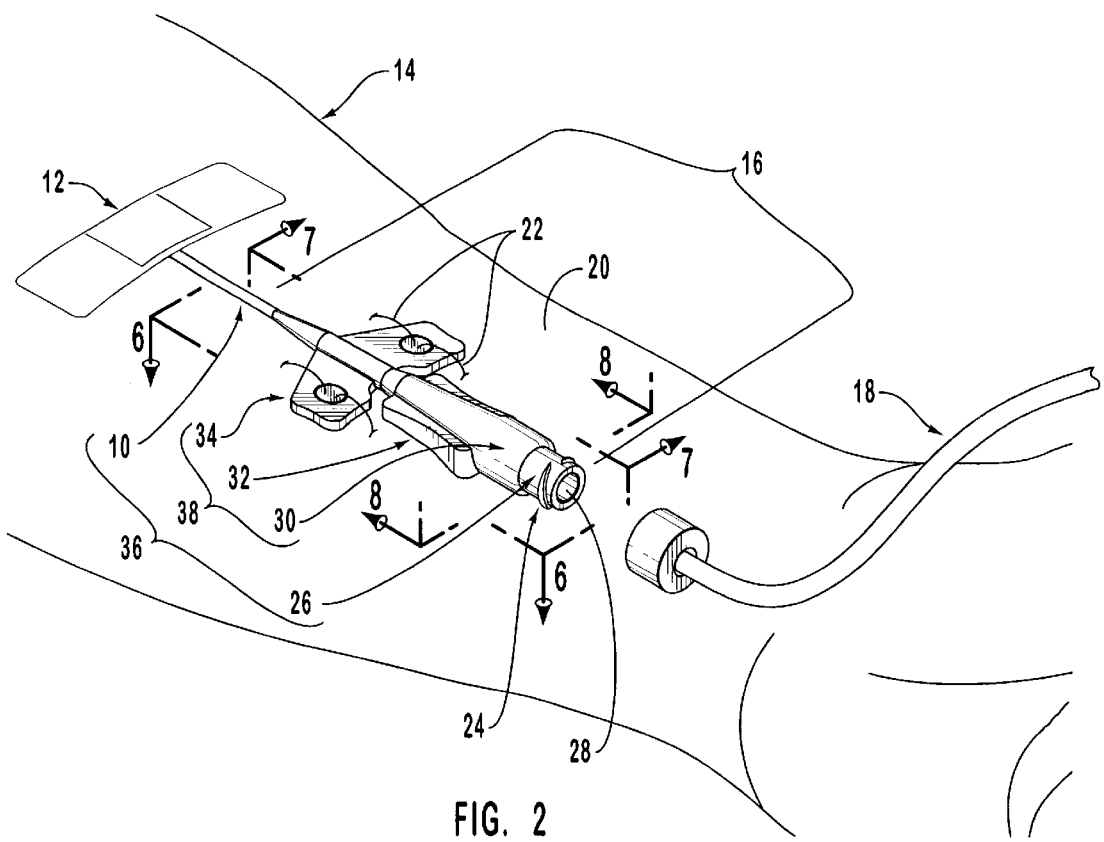
FIG. 2 is an enlarged perspective view of the extracorporeal portion of the implanted catheter of FIG. 1 with the extracorporeal medical tubing shown in FIG. 1 disconnected therefrom to display the coupling and stabilization system of the implanted catheter in the assembled state thereof.

Specific additional features of coupling and stabilization system 16 are illustrated in FIG. 2, wherein extracorporeal tubing 18 has been disconnected from coupling and stabilization system 16, revealing male Luer connector threads 24 at the end of coupling and stabilization system 16 opposite skin exit site 12 and the portion of vascular access catheter 10 visible in FIG. 2. The internal nature of the components of coupling and stabilization system 16 are not immediately apparent from FIG. 2, but such internal structures will be illustrated and discussed subsequently. It will suffice in relation to FIG. 2 to present an overview of selected features of coupling and stabilization system 16 that can be appreciated through external inspection.

Luer connector threads 24 are formed on a catheter coupling hub 26 that encloses the proximal terminus of a longitudinally extending fluid flow lumen. The distal end of catheter coupling hub 26, while not visible in the assembled state of coupling and stabilization system 16 illustrated in FIG. 2, is secured in an enlarged hub receiving socket 30 that is provided on opposite sides of the exterior thereof with concave finger grips 32. Distal of hub receiving socket 30, but separated a distance therefrom, is a pair of laterally extending, coplanar stabilization wings 34 through which suture ties 22 have been stitched to skin 20 of forearm 14.

According to one aspect of the present invention, coupling and stabilization system 16 is comprised of two classes of materials having selected physical properties that are substantially different. Vascular access catheter 10 and catheter coupling hub 26 are secured to each other interior of the other components of coupling and stabilization system 16 that are visible in FIG. 2. Together vascular access catheter 10 and catheter coupling hub 26 comprise a catheter assembly 36. Catheter assembly 36 is comprised of a first class of biocompatible materials that is appropriate for the conditions to which the implanted portion of vascular access catheter 10 is exposed in the cardiovascular system or in the tissues of a patient. The first class of materials must, in addition, be suited to the environment in which the extracorporeal portion of implanted vascular access catheter 10 is disposed and utilized outside the body of the patient. Lumen 28 should thus be enclosed in a conduit of relatively tough biocompatible material that extends from catheter coupling hub 26 through vascular access catheter 10 to the distal end thereof that is not visible in FIG. 2, but that is disposed at a location in the vascular system of the patient at which repeated therapeutic activity is to be conducted. Various thermoplastic materials are satisfactory for use as such a first class of materials in the fabrication of the components of catheter assembly 36.

Typically, catheter coupling hub 26 is a very rigid structure comprised of a much harder material than is catheter 10. Nonetheless, both of these components of catheter assembly 36 can be fabricated from a thermoplastic material, such as polyurethane, provided that the hardness of each respective component is maintained within acceptable ranges through the use of differing types of polyurethane.

Catheter 10 should has a hardness in a range from about 74 Shore A durometer to about 65 Shore D durometer. Most broadly, the hardness of catheter 10 is in a range from about 50 Shore A durometer to about 84 Shore D durometer. It is also acceptable within the scope of the teachings of the present invention to fabricate catheter 10 by coextruding an inner layer that is immediately adjacent to and defining of the lumen in catheter 10 with an outer layer on the exterior thereof that is comprised of a softer material than the inner layer.

Coupling hub 26 should by comparison be generally much harder. For example, coupling hub 26 should have a hardness in a range in excess of 50 Shore D durometer. More narrowly, however, coupling hub 26 will perform adequately with a hardness in a range of from about 80 Shore D durometer to about 84 Shore D durometer. Under appropriate circumstances, materials other than polyurethane can serve adequately as materials from which to fabricate either element of catheter assembly 36. Such alternative materials include polyvinylchloride, nylon, polyester, castable epoxy, and even metals, such as stainless steel or titanium.

Hub receiving socket 30, finger grips 32, and stabilization wings 34 are external features of an elastomeric stabilization sleeve 38. Stabilization sleeve 38 encircles the distal end of catheter coupling hub 26, which is not visible in FIG. 2, and also encircles a portion of the proximal end of vascular access catheter 10 that is adjacent to catheter coupling hub 26 but that is also not visible in FIG. 2. These portions of catheter assembly 36 do, however, appear in FIG. 3, in relation to which these portions of catheter assembly 36 are identified by reference characters and discussed in further detail subsequently. In contrast to catheter assembly 36, stabilization sleeve 38 is comprised of a second class of materials that is soft, flexible, and suitable for skin contacting applications.

Currently, the material of choice for stabilization sleeve 38 is a thermoset material, such as biocompatible silicone. The hardness of stabilization sleeve 38 should be in a broad range of from about 35 Shore A durometer to about 100 Shore A durometer. More specifically, the hardness of stabilization sleeve 38 should be in a range of from about 74 Shore A durometer to about 80 Shore A durometer. The fabrication of stabilization sleeve 38 is not, however, limited to such materials, as the use of polyurethane possessed of appropriate hardness properties is also contemplated for use as stabilization sleeve 38. In any case, it is recommended that the material of which sleeve 38 is fabricated be a material that can be cleaned using a substance selected from the group comprising alcohol, acetone, and polyethylene glycol.

One of the selected physical properties that may advantageously be made to contrast between catheter assembly 36 and stabilization sleeve 38 is the visual appearance of each. It is possible, for example, to use a single color of material for all sizes of catheter 10 used in a catheter assembly, such as catheter assembly 36. The material used for the corresponding stabilization sleeve 38 with each different size of catheter may, however, be rendered in a different hue in order to facilitate the ready identification according to a code of colors of the size of the catheter being utilized.

Figure 3:
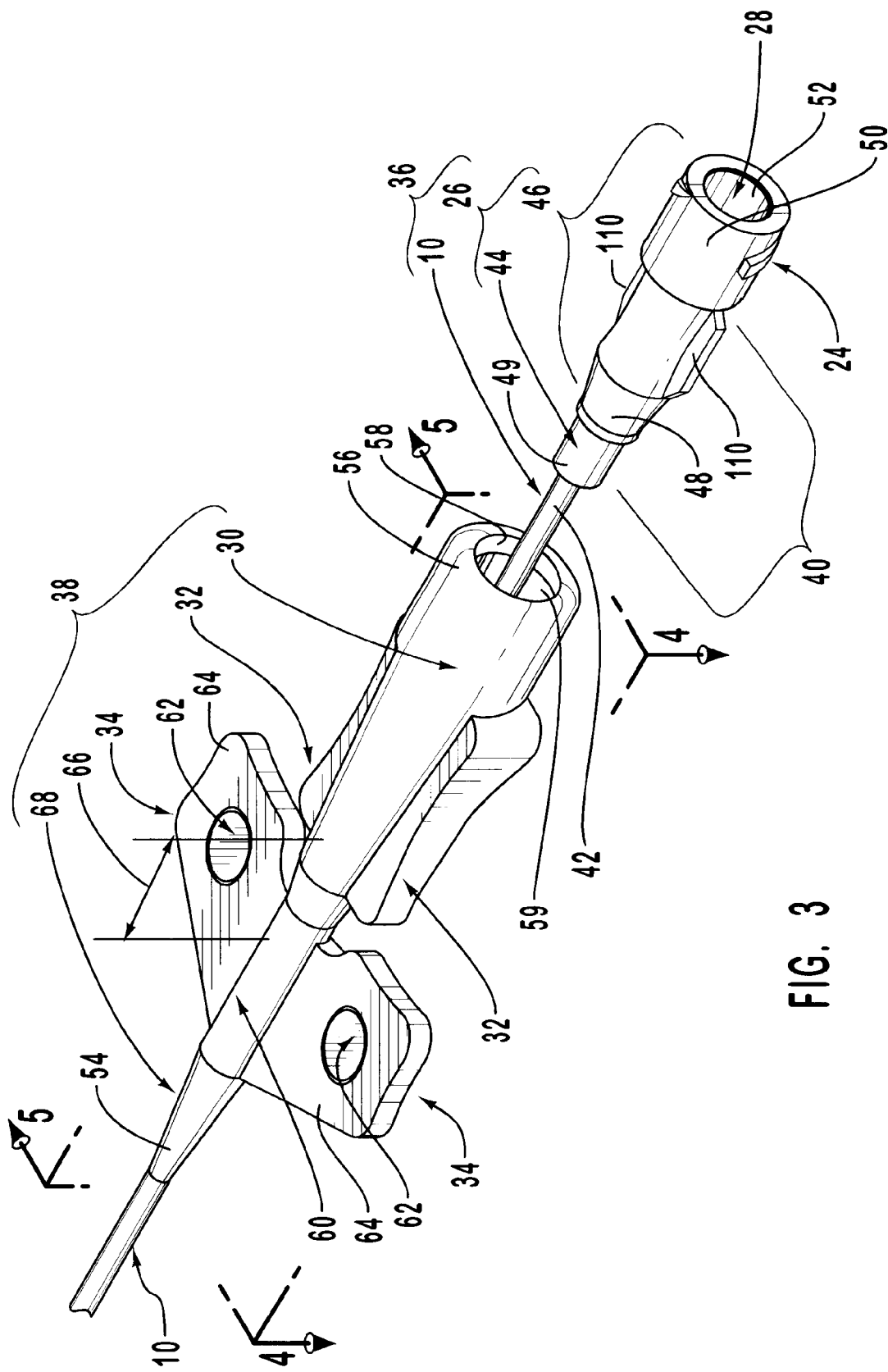
FIG. 3 is an enlarged, partially disassembled perspective view of the catheter assembly and a first embodiment of a stabilization sleeve of the coupling and stabilization system of FIG. 2.

The relationships among the components of coupling and stabilization system 16 are presented with enhanced clarity in FIG. 3. There, catheter assembly 36, which is normally permanently secured to stabilization sleeve 38 at catheter coupling hub 26, only has with vascular access catheter 10 been withdrawn proximally from hub receiving socket 30, providing a disassembled perspective view of coupling and stabilization system 16. It is apparent, as a result, that catheter coupling hub 26 is an elongated structure that is secured at the distal end 40 thereof to the proximal end 42 of vascular access catheter 10. In actuality, catheter coupling hub 26 includes a pair of components. These are a catheter receiving stent 44 and a coupling hub body 46. Catheter receiving stent 44 surrounds and is attached to the outer surface of the terminus of proximal end 42 of vascular access catheter 10. Coupling hub body 46 is attached at the distal end 48 thereof to the outer surface 49 of receiving stent 44. These interconnections can be effected either with an adhesive or, if all constituents of catheter assembly 36 are thermoplastic materials, by heat-induced welding.

The proximal end 50 of coupling hub body 46 carries Luer connector threads 24 that encircle the proximal end 52 of lumen 28.

FIG. 3 also reveals that the portions of catheter assembly 36 not otherwise visible in the assembled state of coupling and stabilization system 16 illustrated in FIGS. 1 and 2 are in the assembled state of coupling and stabilization 16 encircled by stabilization sleeve 38. According to one aspect of the present invention, stabilization sleeve 38 is an elongated tube that has a distal end 54, a proximal end 56, and a passageway 58 extending longitudinally therebetween. Passageway 58 is so sized as to slideably receive catheter 10, but the minimum diameter of passageway 58 is less than the maximum outer diameter of catheter coupling hub 26. The inner diameter of passageway 58 in stabilization sleeve 38 at proximal end 56 thereof corresponds generally in size to the exterior of proximal end 50 of coupling hub body 46. A generally cylindrical hollow 59 is formed within hub receiving socket 30 capable of enclosing the full length of catheter assembly 36 other than the portion thereof that carries Luer connector threads 24. As a result, in the assembled state of coupling and stabilization system 16, distal end 48 of coupling hub body 46 each made, for example, of polyurethane materials abuts a portion of the interior of stabilization sleeve 38, while vascular access catheter 10 having a much smaller diameter than the outer diameter of coupling hub body 46 is slideably disposed in the balance of passageway 58 in stabilization sleeve 38.

Other features of the exterior of stabilization sleeve 38 should receive mention relative to FIG. 3. According to an aspect of the present invention, the exterior of a sleeve, such as stabilization sleeve 38, includes attachment means for securing the sleeve at a predetermined position and in a predetermined orientation on the skin of a patient. As shown in FIG. 3, by way of example of structure capable of performing the function of such an attachment means are a pair of stabilization wings 34.

Each of stabilization wings 34 can be seen to comprise a planar structure that extends laterally from opposite sides of stabilization sleeve 38 at an attachment location 60. While the configuration of stabilization wings 34 will be explored in greater detail subsequently, it can be observed that a suture recess 62 is formed in upper surface 64 of each of stabilization wings 34. At suture recess 62, the thickness of stabilization wings 34 is a minimum, thereby to facilitate, if desired, the stitching of coupling and stabilization system 16 to the skin of the patient using suture ties 22 in the manner shown in FIGS. 1 and 2. Stabilization wings 34 and stabilization sleeve 38 may advantageously be integrally formed of a single material.

As attachment location 60 is distanced longitudinally along stabilization sleeve 38 from hub receiving socket 30, a strain relief region 66 is formed in stabilization sleeve 38 intermediate attachment location 60 and hub receiving socket 30. Strain relief region 66 of stabilization sleeve 38 has in various embodiments thereof a length greater than 0.32 inches. In other embodiments, however, the length of strain relief region 66 has been greater than only 0.20 inches and at the very least greater than 0.12 inches. A frustoconical strain relief nose 68 is located on stabilization sleeve 38 distal of attachment location 60.

Figure 4:
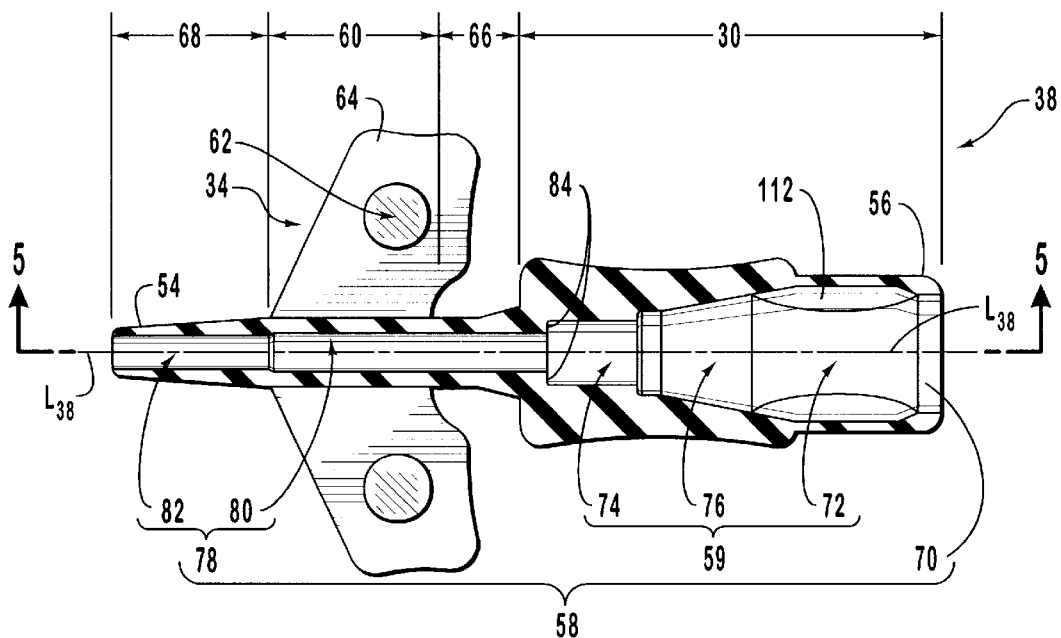
FIG. 4 is a plan view in cross section of the stabilization sleeve of FIG. 3 taken along section line 4—4 shown therein.

The interior structure of stabilization sleeve 38 is illustrated in cross section in FIG. 4. There, each of strain relief nose 68, attachment location 60, strain relief region 66, and hub receiving socket 30 can be correlated with corresponding interior structures of stabilization sleeve 38 along the length of passageway 58.

At proximal end 56 of stabilization sleeve 38, proximal entryway 70 of passageway 58 affords access to hollow 59 within hub receiving socket 30. Hollow 59 includes a generally large diameter cylindrical region 72 at proximal entryway 70, a smaller diameter cylindrical region 74 at the opposite distal end of hollow 59, and a frustoconical medial section 76 therebetween. A yet smaller diameter, two-stage distal portion 78 of passageway 58 extends from cylindrical region 74 of hollow 59 to the open distal end 54 of stabilization sleeve 38 at the apex of strain relief nose 68. Distal portion 78 of passageway 58 includes a larger bore section 80 that passes through attachment location 60 and strain relief region 66, as well as a small bore region 82 that extends through strain relief nose 68. Although small bore region 82 of distal portion 78 of passageway 58 has the smallest inner diameter of any component of passageway 58, the inner diameter of small bore region 82 is nonetheless sufficiently large to slideably house vascular access catheter 10 therein.

On the other hand, it is in hollow 59, and against the distal end wall 84 of cylindrical region 74 in particular, that receiving stent 44 of catheter coupling hub 26 abuttingly engages a structure in passageway 58 in the assembled condition of coupling and stabilization system 16. Significantly, according to one aspect of the present invention, stabilization sleeve 38 is affixed to catheter assembly 36 only at hollow 59 using, by way of example, a room temperature vulcanizing silicone rubber adhesive. The portion of catheter assembly 36 distal of hollow 59 is slideably disposed in distal portion 78 of passageway 58.

Figure 5:
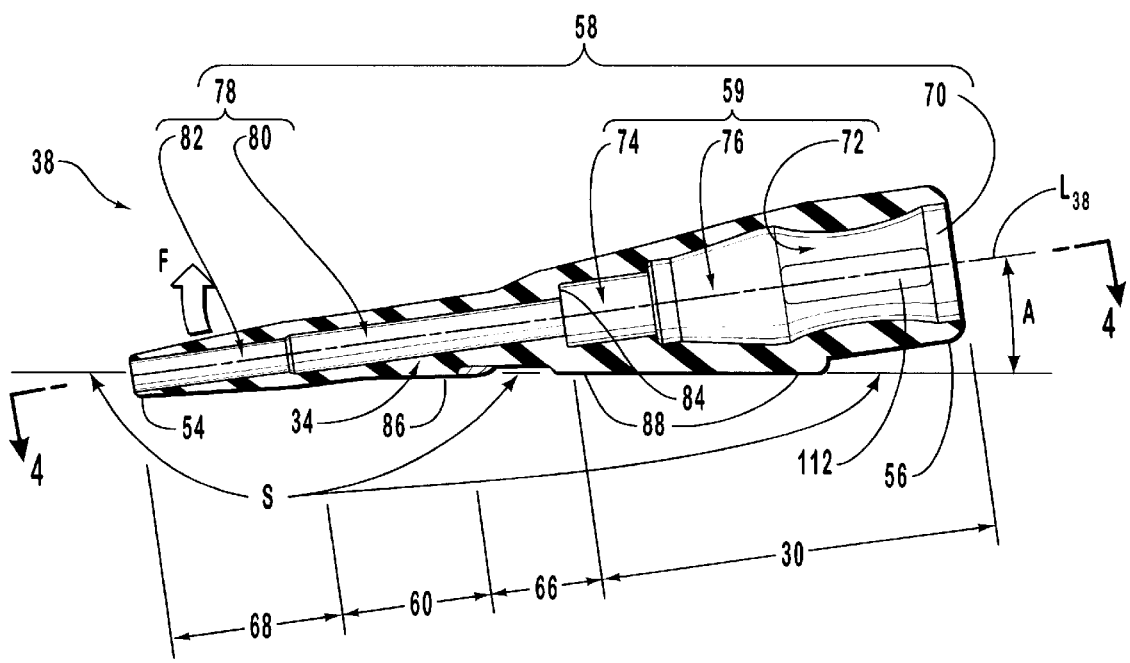
FIG. 5 is an elevation view in cross section of the stabilization sleeve of FIG. 3 taken along section line 5—5 shown therein.

One aspect of the configuration of stabilization sleeve 38 is best addressed relative to the elevation cross section of stabilization sleeve 38 shown in FIG. 5. There, at attachment location 60, the lower patient contact surfaces 86 of stabilization wings 34 can be seen. Proximal of attachment location 60, the exterior of stabilization sleeve 38 in the vicinity of hub receiving socket 30 is correspondingly formed into a generally planar skin contact surface 88 that is disposed in a coplanar relationship with patient contact surface 86 on the same side of stabilization sleeve 38 therewith. The orientation of the common plane defined by patient contact surface 86 and skin contact surface 88 is such that when patient contact surface 86 and skin contact surface 88 engage the skin S of a patient, longitudinal axis $L_{38}$ of stabilization sleeve 38 is elevated relative to that common plane at an elevation angle A. In so doing, it is intended according to teachings of the present invention that the elastomeric nature of the material from which stabilization sleeve 38 is comprised will permit strain relief nose 68 to be displaced upwardly in a direction shown in FIG. 5 by arrow F, so that the exterior of strain relief nose 68 on the same side of stabilization sleeve 38 as patient contact surface 86 and skin contact surface 88 will become coplanar therewith, resting on skin S of the patient in the manner shown, for example in FIG. 7, subsequently.

FIG. 6 illustrates the relationship between the exterior features of catheter assembly 36 and the interior walls of passageway 58. As illustrated there, receiving stent 44 encircles the exterior of vascular access catheter 10, while coupling hub body 46 is attached to the exterior of receiving stent 44. Together, these elements comprise catheter assembly 36. Lumen 28 extending longitudinally through catheter assembly 36 includes catheter lumen 90 of vascular access catheter 10 and enlarged proximal terminus 92 at proximal end 50 of coupling hub body 46.

The generalized structural elements of stabilization wings 34 are best investigated in relation to the depictions in FIG. 6. There, each of stabilization wings 34 can be seen to comprise an anchor root 96 that is secured directly to attachment location 60. The width of anchor root 96 is the extent of anchor root 96 measured parallel to longitudinal access $L_{38}$ of stabilization sleeve 38. An anchor wing 98 is secured to the end of anchor root 96 remote from stabilization sleeve 38. The width of anchor wing 98 is also measured parallel to longitudinal axis $L_{38}$ of stabilization sleeve 38. Anchor wing 98 is bounded by a trailing edge 100 oriented toward hub receiving socket 30, a leading edge 102 on the opposite side of anchor wing 98 from trailing edge 100, and a tip 104 extending between leading edge 102 and trailing edge 100 remote from stabilization sleeve 38. In the embodiment of stabilization wing 34 illustrated in FIG. 6, trailing edge 100 and tip 104 are slightly convex, while leading edge 102 is linear, trailing edge 100 is oriented at an acute angle $A_{100p}$ to longitudinal axis $L_{38}$ of stabilization sleeve 38 distal of attachment location 60, and leading edge 102 is oriented at an acute angle $A_{102p}$ to longitudinal axis $L_{38}$ of stabilization sleeve 38 proximal of attachment location 60. A strain relief region extension notch 106 is formed in trailing edge 100 of stabilization wing 34, thus causing the width of anchor root 96 to be less than the width of anchor wing 98.

FIG. 7 illustrates many of the same structures already discussed in relation to FIG. 6. On the left side of FIG. 7, however, enabled by the resiliency thereof, strain relief nose 68 has been displaced in a direction illustrated by arrow F, so that the exterior of strain relief nose 68 on the same side of stabilization sleeve 38 as patient contact surface 86 and skin contact surface 88 rests in a coplanar relationship therewith on the skin S of a patient. While catheter coupling hub 26 is fixedly engaged within hub receiving socket 30 of stabilization sleeve 38, catheter 10 distal of and adjacent to catheter coupling hub 26 extends slideably through distal portion 78 of passageway 58. As a result, catheter 10 at strain relief nose 68 is not displaced in the direction of arrow F or to any similar degree as strain relief nose 68. Catheter 10 comes to be disposed within small bore region 82 and large bore region 80 of distal portion 78 of passageway 58 in a nonconcentric relationship. The flexibility of the material of which stabilization sleeve 38 is comprised in combination with the slidable disposition of vascular access catheter 10 within distal portion 78 of passageway 58 in stabilization sleeve 38 permits strain relief nose 68 and, to an extent, attachment location 60 to afford relief to catheter 10 from lateral types of bending strain.

As a result of the configuration of the portion of stabilization sleeve 38 proximal of attachment location 60, the longitudinal axis $L_{38}$ of stabilization sleeve 38 and the longitudinal axis of lumen 28 at the proximal end of catheter assembly 36 are disposed at an inclination angle A to the skin S of the patient.

Figure 8:
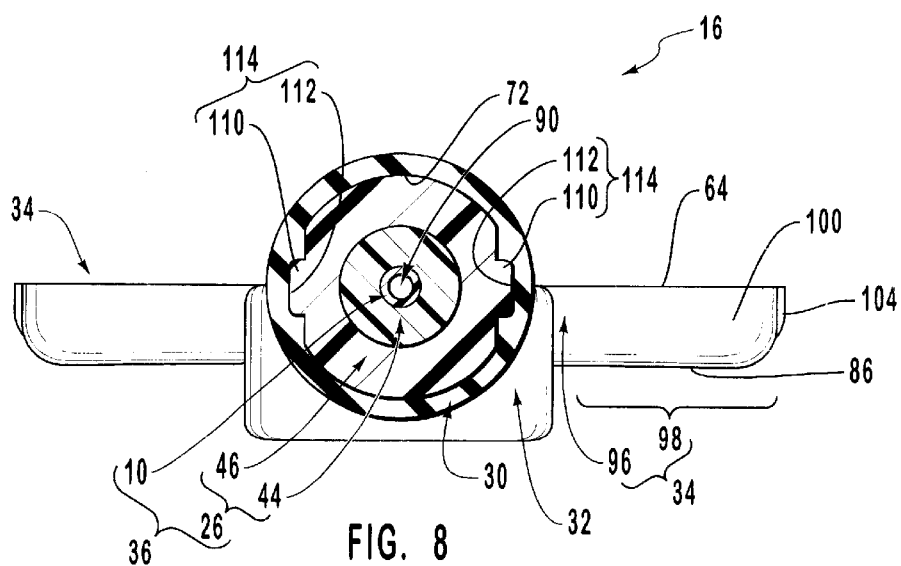
FIG. 8 is a transverse elevation view in cross section of the assembled state of the stabilization system shown in FIG. 2 taken along section line 8—8 therein.
Figure 8A:
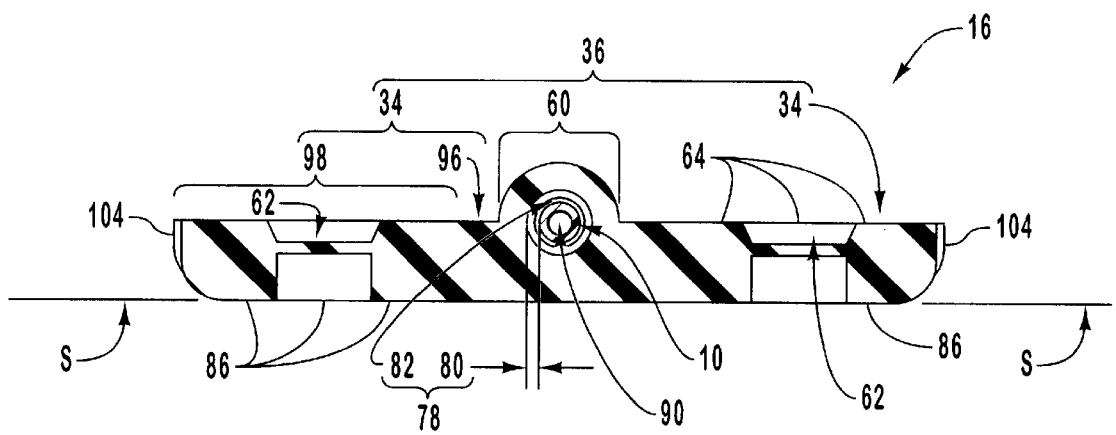
FIG. 8A is a transverse elevation cross section of the assembled state of the stabilization system shown in FIG. 2 taken along section line 8A—8A appearing in each of FIGS. 6 and 7.

According to one aspect of the present invention, in a catheter coupling and stabilization system, such as coupling and stabilization system 16, cooperating alignment means are provided for facilitating and stabilizing a predetermined rotational relationship between a stabilization sleeve of that system and the catheter coupling hub of the catheter assembly associated therewith. By way of example and not limitation, as illustrated to best advantage in FIG. 8, the exterior of catheter coupling hub 26 is provided with an upstanding, longitudinally extending alignment rib 110 that is received in correspondingly longitudinally aligned alignment rib receiving slot 112 formed in the wall of passageway 58 at cylindrical region 72 of hollow 59. Together, alignment rib 110 and alignment rib receiving slot 112 function as a key and keyway system 114.

Figure 9A:
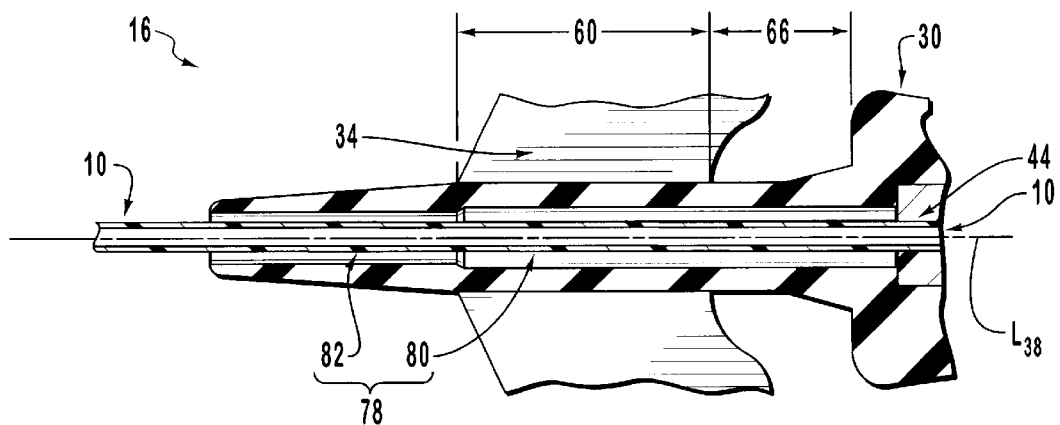
FIG. 9A is an enlarged detail of a portion of the coupling and stabilization system shown in FIG. 6.
Figure 9B:
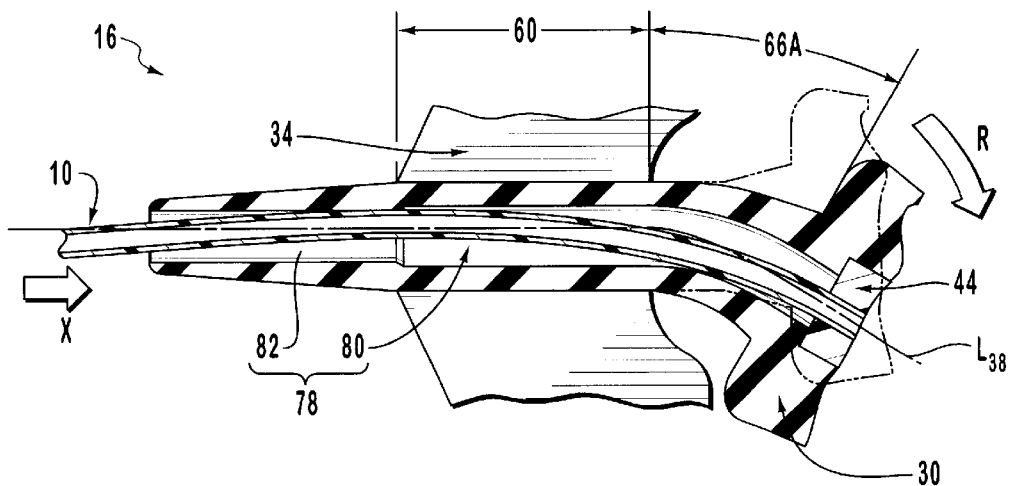
FIG. 9B is an illustration of the interaction of the strain relief features of the coupling and stabilization system of FIG. 9A with the portion of the catheter enclosed therein under conditions of strain in which the portion of the system in the right of the figure is displaced in a downward direction.
Figure 9C:
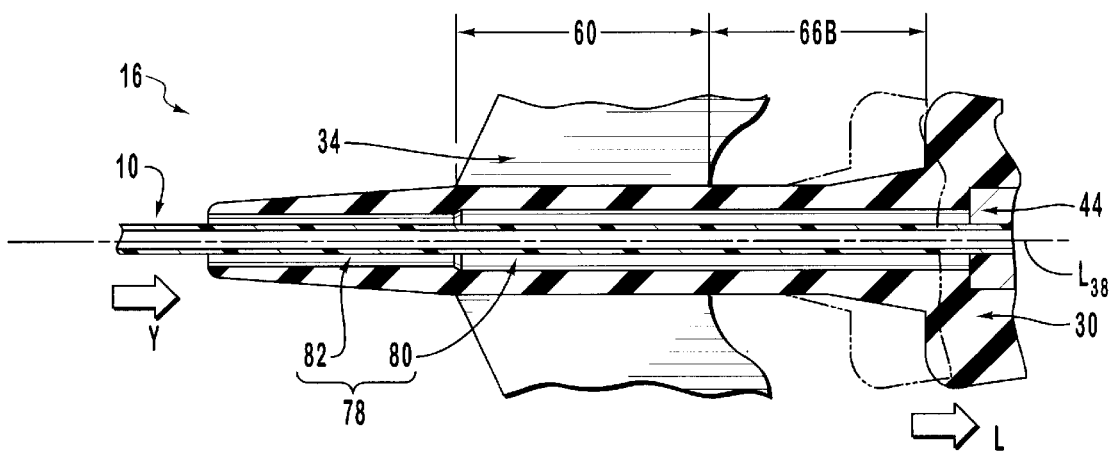
FIG. 9C is an illustration of the interaction of the strain relief features of the system of FIG. 9A with the portion of the catheter enclosed therein under conditions of strain in which the portion of the system in the right of the figure is displaced to the right.

FIGS. 9A–9C depict the effects on the relationship of structures in the interior of coupling and stabilization system 16 resulting when stabilization wings 34 are secured to the skin of a patient and movement parallel to the skin is imparted to catheter coupling hub 26.

FIG. 9A is an enlarged detail of a portion of coupling and stabilization system 16 illustrated in FIG. 6. Salutary effects of specific aspects of coupling and stabilization system 16 will be explored. Stabilization sleeve 38 is comprised of an elastomeric material. Catheter 10 is slideably disposed in distal portion 78 of passageway 58 in stabilization sleeve 38. Receiving stent 44 is permanently secured in hub receiving socket 30. Strain relief region 66 is advantageously positioned between attachment location 60 and the distal portion of catheter coupling hub 26. According to an aspect of the present invention a sleeve, such as stabilization sleeve 38, includes resilient means for reducing motion imparted to the skin of a patient by stabilization wings, such as stabilization wings 34, due to motion imparted to a catheter coupling hub, such as catheter coupling hub 26. As shown in FIG. 9A, an example of structure capable of performing the function of such a resilient means is strain relief region 66.

In FIG. 9B, a force has been applied to hub receiving socket 30 that has displaced hub receiving socket 30 and receiving stent 44 therein downwardly from the original position thereof indicated in phantom in a direction indicated by arrow R. The ability to freely pivot hub receiving socket 30 in this manner contributes to the ease with which extracorporeal tubing and medical equipment can be engaged to the proximal end of a catheter incorporating a coupling and stabilization system according to the present invention. The strain of this type of displacement of hub receiving socket 30 is not, however, communicated directly to the skin S of the patient at stabilization wings 34.

Instead, strain relief region 66 assumes a twisted configuration 66A, and vascular access catheter 10 is drawn along distal portion 78 of passageway 58 in the direction indicated by arrow X. The movement of hub receiving socket 30 as indicated by arrow R does not produce corresponding movement in stabilization wings 34 or in the skin of the patient to which stabilization wings 34 are attached. Furthermore, upon the release of whatever force produced the movement of hub receiving socket 30 indicated by arrow R, the resiliency of strain relief region 66 will restore hub receiving socket 30 to the original position thereof indicated in phantom in FIG. 9B. Catheter 10 will correspondingly return longitudinally in a direction opposite that indicated by arrow X and resume the original position thereof, both in and out of the vascular system.

Similar benefits occur in relation to longitudinal displacements of hub receiving socket 30 with receiving stent 44 fixed therein. Such a situation is illustrated in FIG. 9C. There, a force applied to hub receiving socket 30 has displaced hub receiving socket 30 in the direction indicated by arrow L. Instead of correspondingly displacing stabilization wings 34 or the skin of the patient to which stabilization wings 34 are attached, strain relief region 66 becomes distended into an elongated shape 66B, and vascular access catheter 10 slides freely within distal portion 78 of passageway 58. The strain imposed on hub receiving socket 30 is in effect dissipated or attenuated by strain relief region 66 of stabilization sleeve 38.

Strain relief region 66 affords other advantages as will be discussed in relation to FIGS. 10–10D. These figures illustrate steps in the securement of the extracorporeal portion of a catheter embodying teachings of the present invention to the skin of a patient using medical adhesive tape 120 and coupling and stabilization system 16. The positioning of attachment location 60 for stabilization wings 34 at a distance from hub receiving socket 30 and thus catheter coupling hub 26 permits medical adhesive tape 120 to be used with optimum effectiveness.

Medical adhesive tape 120 has an adhesive side 122 that is shaded in the figures and a nonadhesive side 124 that is free of shading.

Figure 10A:
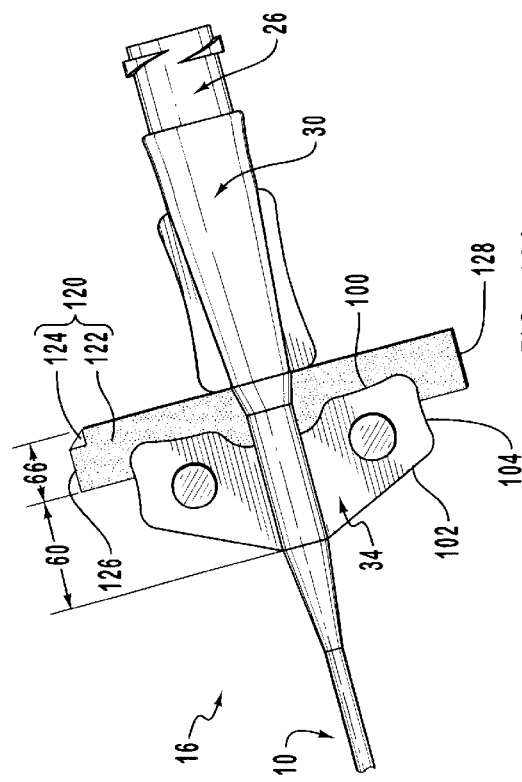
FIG. 10A is a plan view schematic illustration of an initial step in the securement of the extracorporeal portion of a catheter to the skin of a patient using medical adhesive tape and the coupling and stabilization system of FIG. 2.

In FIG. 10A, the first step of this procedure is illustrated. Adhesive side 122 of medical adhesive tape 120 is disposed against the lower side of coupling and stabilization system 16 at strain relief region 66. The free ends 126, 128 of medical adhesive tape 120 extend laterally beyond tips 100 of stabilization sleeves 38, and trailing edges 104 of stabilization sleeves 38 overlie adhesive side 122 of medical adhesive tape 120.

Figure 10B:
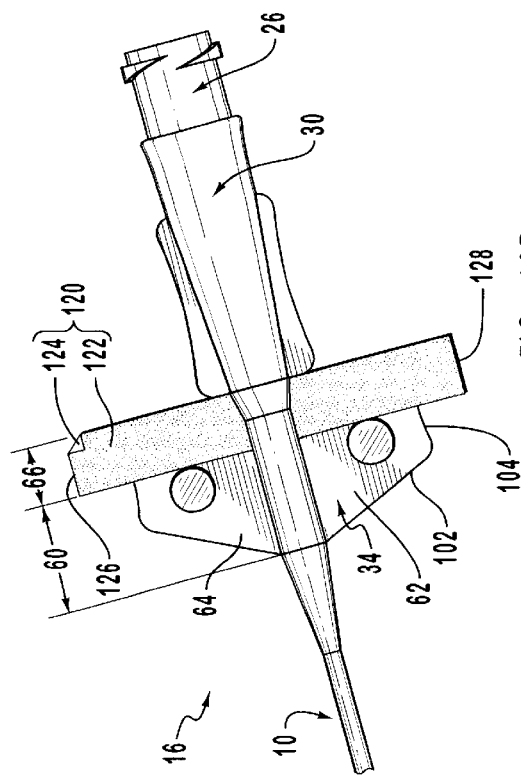
FIG. 10B is a plan view schematic illustration of a second step in the securement of the extracorporeal portion of the catheter of FIG. 10A to the skin of a patient.

This latter situation is then altered in the manner illustrated in FIG. 10B. Free ends 126, 128 of medical adhesive tape 120 are pivoted at strain relief region 66 about and over trailing edges 100 of stabilization wings 34. Medical adhesive tape 120 thus continues unwrinkled to occupy strain relief region 66 between attachment location 60 and hub receiving socket 30.

Figure 10C:
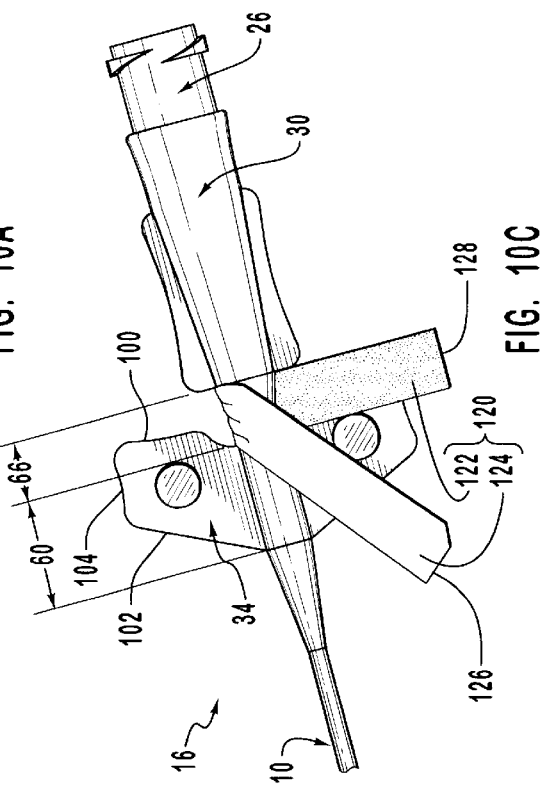
FIG. 10C is a plan view schematic illustration of a third step in the securement of the extracorporeal portion of the catheter of FIG. 10B to the skin of a patient.
Figure 10D:
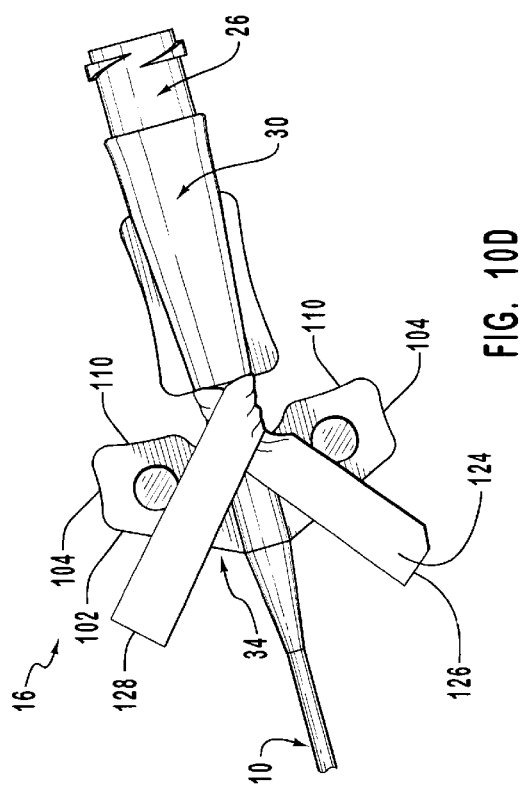
FIG. 10D is a plan view schematic illustration of a final step in the securement of the extracorporeal portion of the catheter of FIG. 1 to the skin of a patient.

As illustrated in FIG. 10C, free end 126 of medical adhesive tape 120 is next crossed over strain relief region 66 and the upper surface 62 of stabilization wing 34 on the opposite side of stabilization sleeve 38.

Finally, the same procedure is undertaken with relation to free end 128 of medical adhesive 120. The results are illustrated in FIG. 1 OD. Through the use of medical adhesive tape 120 as a tie-down material, coupling and stabilization system 16 is firmly secured at attachment location 60 to the skin of the patient. Still, substantial freedom of movement is permitted in hub receiving socket 30 and catheter coupling hub 26, as was discussed relative to FIGS. 9B and 9C. The length of strain relief region 66 contributes to this positive result, as does the slidable disposition of catheter 10 through the portion of stabilization sleeve 38 distal of catheter coupling hub 26.

Figure 11A:
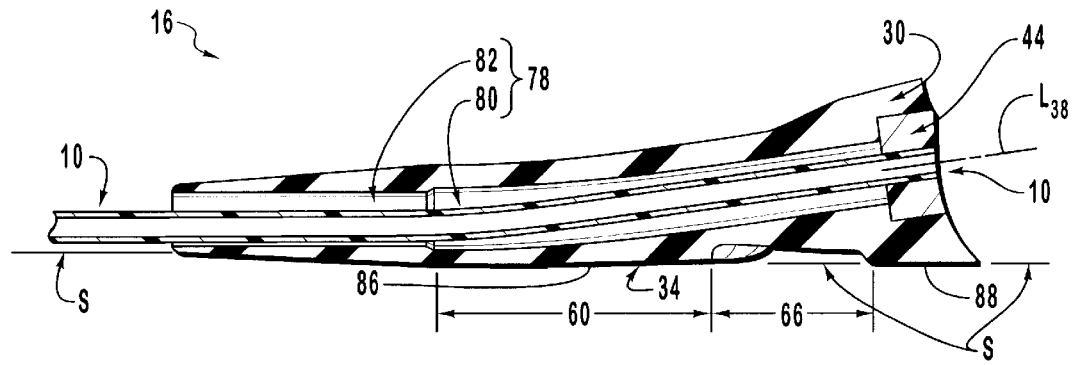
FIG. 11A is an enlarged detail of a portion of the coupling and stabilization system shown in FIG. 7.
Figure 11B:
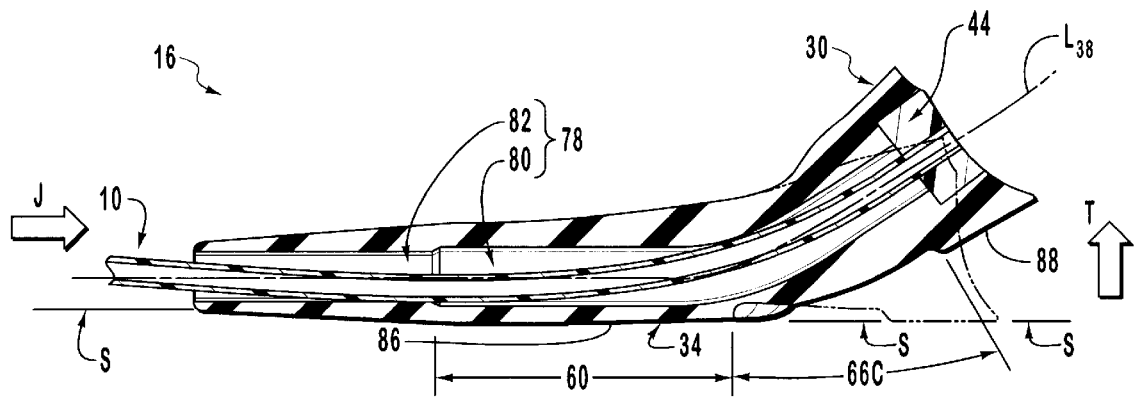
FIG. 11B is an illustration of the interaction of the strain relief features of the system of FIG. 11A with the portion of the catheter enclosed therein under conditions of strain in which the portion of the system in the right of the figure is displaced in a downward direction.
Figure 11C:
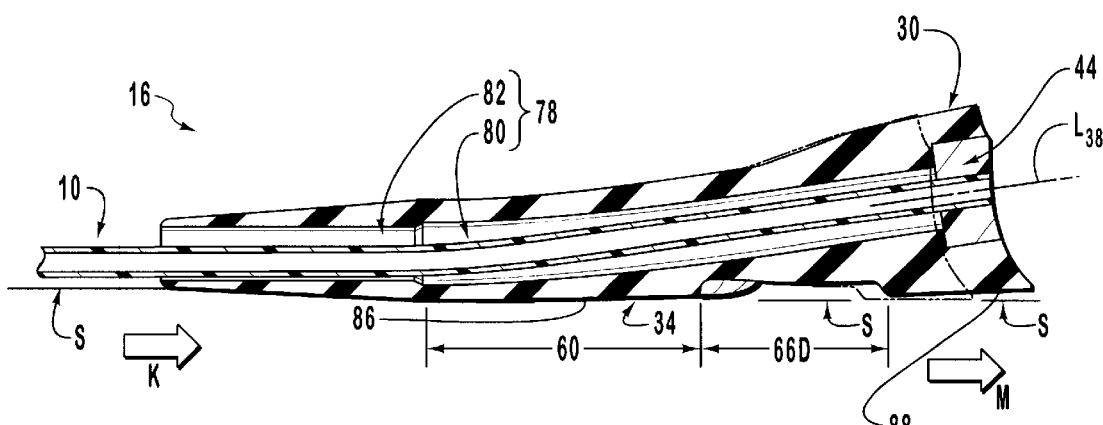
FIG. 11C is an illustration of the interaction of the strain relief features of the system of FIG. 11A with the portion of the catheter enclosed therein under conditions of strain in which the portion of the system in the right of the figure is displaced to the right.

FIGS. 11A–11C depict the effects on the relationship of structures in the interior of coupling and stabilization system 16 as a result of other types of movements than those illustrated in FIGS. 9B and 9C are imparted to catheter coupling hub 26 when stabilization wings 34 are secured to the skin of a patient as, for example, in the manner taught in FIGS. 10A–10D.

FIG. 11A is an enlarged detail of a portion of coupling and stabilization system 16 illustrated in FIG. 7.

In FIG. 11B, a force has been applied to hub receiving socket 30 that has displaced hub receiving socket 30 and receiving stent 44 upwardly in a direction indicated by arrow T from the original position thereof shown in FIG. 11A and indicated in FIG. 11B in phantom. The ability to freely pivot hub receiving socket 30 in this manner contributes to the ease with which extracorporeal tubing and medical equipment can be engaged to the proximal end of a catheter incorporating a coupling and stabilization system according to the present invention. The strain of this type of displacement of hub receiving socket 30 is not, however, communicated directly to the skin S of the patient at stabilization wings 34.

Instead, strain relief region 66 assumes a twisted configuration 66C, and vascular access catheter 10 is drawn along distal portion 78 of passageway 58 in the direction indicated by arrow J. The movement of hub receiving socket 30 as indicated by arrow T does not produce 10 corresponding movements in stabilization wings 34 or in the skin of the patient to which stabilization wings 34 are attached. Furthermore, upon the release of whatever force produced the movement of hub receiving socket 30 indicated by arrow T, the resiliency of strain relief region 66 restores hub receiving socket 30 to the original position thereof indicated in phantom in FIG. 11B. Catheter 10 will correspondingly return longitudinally in the direction opposite that indicated by arrow J and resume the original position thereof, both in and out of the vascular system.

Similar benefits occur in relation to longitudinal lateral displacement of hub receiving socket 30 with receiving stent 44 fixed therein. Such a situation is illustrated in FIG. 11C. There, a force applied to hub receiving socket 30 has displaced hub receiving socket 30 in the direction indicated by arrow M. Instead of correspondingly displacing stabilization wings 34 or the skin of the patient to which stabilization wings 34 are attached, strain relief region 66 becomes distended into an elongated shape 66D, and vascular access catheter 10 slides freely within distal portion 78 of passageway 58. The strain imposed on hub receiving socket 30 is in effect dissipated or intenuated by strain relief region 66 of stabilization sleeve 38.

FIGS. 12A–12D illustrate a number of alternative embodiments of catheter coupling and stabilization systems that incorporate teachings of the present invention and exhibits a variety of configurations of the stabilization sleeves utilized with such systems.

In FIG. 12A, a stabilization sleeve 38A is illustrated. A pair of stabilization wings 140 projects laterally from opposite sides of stabilization sleeve 38A at attachment location 60. Stabilization wing 140 has an anchor root 142 and an anchor wing 144. Trailing edge 146 of stabilization wing 140 is substantially linear and is oriented at an acute angle $A_{146p}$ to longitudinal axis $L_{38A}$ of stabilization sleeve 38A being oriented by contrast at an acute angle $A_{148d}$ to longitudinal axis $L_{38A}$ distal of attachment location 60 proximal of attachment location 60. Leading edge 148 of stabilization wing 140 is substantially straight adjacent to stabilization sleeve 38A, but curving broadly at the end thereof remote from stabilization sleeve 38A to tangentially intersect tip 150 of stabilization wing 150. Tip 104, which is substantially linear, is disposed in a substantially parallel arrangement with longitudinal axis $L_{38A}$ of stabilization sleeve 38A. A notch 152 in trailing edge 146 of stabilization wing 140 results in root 142 of stabilization wing 140 being narrower than anchor wing 144.

In FIG. 12B, yet another stabilization sleeve 3 8B is illustrated. A pair of stabilization wings 154 projects laterally from opposite sides of stabilization sleeve 38B at attachment location 60. Stabilization wing 154 is comprised of an anchor root 156 and an anchor wing 158. Trailing edge 160 of stabilization wing 154 is substantially linear, but is oriented at an acute angle $A_{160d}$ to longitudinal axis $L_{38B}$ of stabilization sleeve 38B distal of attachment location 60. Leading edge 162 of stabilization wing 154 is concave and oriented generally at an acute angle $A_{162p}$ to longitudinal axis $L_{38B}$ of stabilization sleeve 38B proximal of attachment location 60. Tip 164 of stabilization sleeve 154 is linear and disposed at an acute angle with longitudinal axis $L_{38B}$ of stabilization sleeve 38B proximal of attachment location 60. A notch 166 is formed in trailing edge 160 of stabilization wing 154 adjacent to stabilization sleeve 38B.

In FIG. 12C, a stabilization sleeve 38C is illustrated. A pair of stabilization wings 170 project laterally from opposite sides of stabilization sleeve 38C at attachment location 60. Stabilization wing 170 includes an anchor root 172 and an anchor wing 174. Both trailing edge 176 and leading edge 178 of stabilization wing 170 are substantially linear and are oriented perpendicular to longitudinal axis $L_{38C}$ of stabilization sleeve 3 8C. Accordingly, trailing edge 176 and leading edge 178 are parallel, and anchor root 172 has a width that is equal to the width of anchor wing 174. Tip 180 of stabilization wing 170 is substantially linear and is oriented substantially parallel to longitudinal axis $L_{38C}$ of stabilization sleeve 38C.

In FIG. 12D, a stabilization sleeve 38D is illustrated. A pair of stabilization wings 182 projects laterally from opposite sides of stabilization sleeve 38D at attachment location 60. Each of stabilization wings 182 includes an anchor root 184 and an anchor wing 186. Both of trailing edge 188 and leading edge 190 of stabilization wing 182 are substantially linear, and both are oriented at an acute angle to longitudinal axis $L_{38D}$ of stabilization sleeve 38D proximal of attachment location 60. Trailing edge 188 thusly forms an acute angle $A_{188d}$ with that portion of longitudinal axis $L_{38D}$ and leading edge 190 does so at an acute angle $A_{190d}$. Tip 192 of stabilization sleeve 182 is convex. Due to the relative orientation of each of trailing edge 188 and leading edge 190, however, the width of anchor root 184 is actually greater than the width of any portion of anchor wing 186.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An implantable vascular access catheter comprising:
   a. a conduit of relatively tough biocompatible material enclosing a longitudinally extending fluid flow lumen, said conduit having a distal end configured as an elongated flexible catheter for disposition in the vascular system of a patient and a proximal end configured as a catheter coupling hub by which to effect mechanical and fluid interaction with extracorporeal medical equipment;
   b. an elastomeric sleeve suitable for skin contact applications encircling the distal end of said catheter coupling hub and a portion of said conduit distal of and adjacent to said distal end of said catheter coupling hub;
   c. a pair of stabilization wings extending laterally from said sleeve distal of said distal end of said catheter coupling hub; and
   d. resilient means between said distal end of said catheter coupling hub and said stabilization wings for reducing motion imparted to the skin of a patient through said stabilization wings due to motion of said catheter coupling hub, when said stabilization wings are secured to the skin of a patient.

2. A catheter as recited in claim 1, wherein said sleeve is attached to said conduit exclusively at said catheter coupling hub.

3. A catheter as recited in claim 2, wherein said portion of said conduit distal of and adjacent to said distal end of said catheter coupling hub extends slidably through said sleeve.

4. A catheter as recited in claim 1, wherein said portion of said conduit distal of and adjacent to said distal end of catheter coupling hub extends slidably through said sleeve.

5. A catheter as recited in claim 1, wherein the hardness of said catheter coupling hub is greater than the hardness of said conduit.

6. A catheter as recited in claim 1, wherein said catheter coupling hub is comprised of polyurethane.

7. A catheter as recited in claim 1, wherein said sleeve comprises silicone.

8. A catheter as recited in claim 1, wherein:
   a. said stabilization wings are generally coplanar, each of said stabilization wings having an upper surface and a lower patient contact surface on the opposite side of each of said stabilization wings therefrom;
   b. the exterior of said sleeve proximally of said stabilization wings is formed into a generally planar skin contact surface disposed on the same side of said sleeve as said patient contact surfaces of said stabilization wings; and
   c. said sleeve at and proximal of said stabilization wings is so configured that when said patient contact surfaces of said stabilization wings and said skin contact surface of said sleeve engage the skin of a patient, the longitudinal axis of said conduit at said proximal end thereof is elevated at an angle to the skin of the patient.

9. A catheter as recited in claim 1, wherein said stabilization wings and said sleeve are integrally formed of a single material.

10. A catheter as recited in claim 1, wherein said resilient means comprises a strain relief region of said sleeve.

11. A catheter coupling and stabilization system for the extracorporeal portion of an implant able catheter, said system comprising:
    a. a catheter assembly comprised of a first class of materials, said catheter assembly comprising:
       i. an elongated flexible catheter having a proximal end and a distal end; and
       ii. a catheter coupling hub, the distal end of said catheter coupling hub being secured to said proximal end of said catheter; and
    b. a stabilization sleeve encircling said distal end of said catheter coupling hub and a portion of said proximal end of said catheter immediately adjacent thereto, said stabilization sleeve having a passageway extending longitudinally therethrough, said distal end of said catheter coupling hub being secured in the proximal end of said passageway with said portion of said proximal end of said catheter immediately adjacent thereto extending therefrom through said passageway, said stabilization sleeve being comprised of a second class of materials having selected physical properties substantially different from corresponding selected physical properties of said first class of materials, and said stabilization sleeve comprising:
       i. a pair of stabilization wings extending from opposite sides of said stabilization sleeve distal of said distal end of said catheter coupling hub; and
       ii. a strain relief region between said catheter coupling hub and said stabilization wings, movement of said catheter coupling hub relative to said stabilization wings being facilitated by said strain relief region when said stabilization wings are secured to the skin of a patient.

12. A system as recited in claim 11, wherein said first class of materials comprises thermoplastic materials that are durable relative to conditions to which the implanted portion of a cardiovascular access catheter is exposed in the cardiovascular system or the tissues of a patient and relative to the environment in which the extracorporeal portion of an implanted catheter is disposed and utilized.

13. A system as recited in claim 12, wherein said first class of materials comprises polyurethane materials.

14. A system as recited in claim 13, wherein:
    a. said catheter is comprised of a first polyurethane material; and
    b. said catheter coupling hub is comprised of a second polyurethane material, said first polyurethane material being softer than said second polyurethane material.

15. A system as recited in claim 11 wherein said second class of materials comprises soft, flexible materials suitable for skin contacting applications.

16. A system as recited in claim 15, wherein said second class of materials comprises thermoset materials.

17. A system as recited in claim 16 wherein said second class of materials comprises biocompatible silicone materials.

18. A system as recited in claim 11, wherein said stabilization sleeve further comprises:
   a. an elongated tube having proximal and distal ends, said passageway of said stabilization sleeve extending longitudinally therebetween; and
   b. a hub receiving socket formed from said passageway at said proximal end of said tube, said distal end of said catheter coupling hub being secured in said hub receiving socket, said stabilization wings extending laterally from opposite sides of said tube distal of said hub receiving socket.

19. A system as recited in claim 18, wherein the wall of said passageway at said hub receiving socket and the exterior of said catheter coupling hub are provided with cooperating alignment means for facilitating and stabilizing a predetermined rotational relationship between said stabilization sleeve and said catheter coupling hub, when said distal end of said catheter coupling hub is secured in said hub receiving socket.

20. A system as recited in claim 19, wherein said alignment means comprises:
   a. an elongated alignment rib upstanding on the exterior of said catheter coupling hub, said alignment rib being oriented generally parallel to the longitudinal axis of said catheter assembly; and
   b. an alignment rib receiving slot formed in said wall of said hub receiving socket, said receiving slot being oriented generally parallel to the longitudinal axis of said stabilization sleeve.

21. A system as recited in claim 18, wherein radially opposed finger grips are provided on the exterior of said tube at said hub receiving socket.

22. A system as recited in claim 18, further comprising a strain relief nose located distal of said attachment location.

23. A system as recited in claim 22, wherein the diameter of said passageway at said strain relief nose is greater than or equal to the outer diameter of said catheter.

24. A system as recited in claim 22, wherein the exterior of said strain relief nose is frustoconical.

25. A system as recited in claim 18, wherein each of said stabilization wings is provided with a suture recess at which the thickness of each respective of said stabilization wings is a minimum.

26. A system as recited in claim 18, wherein a strain relief region extension notch is formed in the edge of each of said stabilization wings adjacent to said strain relief region.

27. A system as recited in claim 11, wherein said catheter coupling hub comprises:
   a. a catheter receiving stent encircling the outer surface of said proximal end of said catheter; and
   b. a hub body encircling the outer surface of said receiving stent.

28. A system as recited in claim 27, wherein said receiving stent is attached to said proximal end of said catheter and to said catheter coupling hub with an adhesive.

29. A system as recited in claim 27, wherein said receiving stent is welded to said proximal end of said catheter and to said catheter coupling hub.

30. A system as recited in claim 11, wherein:
   a said first class of materials comprises hard polyurethane materials, and
   b. said second class of materials comprises soft polyurethane materials.

31. A system as recited in claim 30, wherein:
   a. said catheter is comprised of a first hard polyurethane material; and
   b. said catheter coupling hub is comprised of a second hard polyurethane material, said first hard polyurethane material being softer than said second hard polyurethane material.

32. A system as recited in claim 11, wherein said first class of materials comprises castable epoxy materials.

33. A system as recited in claim 11, wherein:
   a. said first class of materials comprises polyurethane materials; and
   b. said second class of materials comprises biocompatible silicone materials.

34. A system as recited in claim 11, wherein each of said stabilization wings comprises:
   a. a trailing edge oriented toward the proximal end of said stabilization sleeve; and
   b. a notch formed in said trailing edge of each of said stabilization wings adjacent said stabilization sleeve.

35. A catheter coupling and stabilization system for the extracorporeal portion of an implantable catheter, said system comprising:
   a. a catheter having a proximal end and a distal end;
   b. a catheter coupling hub, the distal end of said catheter coupling hub being secured to said proximal end of said catheter; and
   c. a stabilization sleeve encircling said distal end of said catheter coupling hub and a portion of said proximal end of said catheter immediately adjacent thereto, said stabilization sleeve comprising:
      i. an elongated tube having a proximal end, a distal end, and a passageway extending longitudinally therebetween, said distal end of said catheter coupling hub being secured in said passageway at said proximal end of said tube;
      ii. attachment means for securing said tube at a predetermined position and in a predetermined orientation to the skin of a patient, said attachment means being located on the exterior of said tube distal of said catheter coupling hub; and
      iii. a strain relief region between said catheter coupling hub and said attachment means, movement of said catheter coupling hub relative to said attachment means being facilitated by said strain relief region.

36. A system as recited in claim 35, wherein said attachment means comprises a pair of stabilization wings extending laterally from said tube.

37. A system as recited in claim 35, wherein said attachment means comprises a planar stabilization wing extending laterally from said tube and being disposed generally parallel to the longitudinal axis of said tube, said stabilization wing comprising:
   a. a leading edge oriented toward said distal end of said tube;
   b. a trailing edge oriented toward said proximal end of said tube;
   c. a tip extending between said leading edge and said trailing edge remote from said tube; and
   d. a notch formed through said trailing edge of said stabilization wing adjacent said tube.

38. A system as recited in claim 35, wherein said catheter is a single lumen catheter.

\* \* \* \* \*

UNITED STATES PATENT AND TRADEMARK OFFICE
CERTIFICATE OF CORRECTION

PATENT NO. : 6,332,874 B1  
DATED : December 25, 2001  
INVENTOR(S) : Kenneth A. Eliasen et al.

Page 1 of 2

It is certified that error appears in the above-identified patent and that said Letters Patent is hereby corrected as shown below:

Title page,  
Item [63], Related U.S. Application Data, change "April 20, 1999" to -- July 22, 1998 --; and  
Item [57], ABSTRACT,  
Line 8, change "extends" to -- extend --.

Column 1,  
Line 7, delete "appl. Ser. No. 29/091063, filed Apr. 20, 1999 now U.S.";  
Line 14, after "catheters" insert -- , --;

Column 4,  
Line 52, change "explanation" to -- explantation --;

Column 5,  
Line 17, after "occasion" insert -- , --;  
Line 67, delete the comma;

Column 6,  
Line 35, change "extends" to -- extend --;

Column 9,  
Line 25, delete "thus";  
Line 41, delete "should";

Column 10,  
Line 39, delete "only";  
Line 47, after "hub body 46" insert -- , each made, for example, of polyurethane materials --;

Column 11,  
Lines 11 and 12, delete "each made, for example, of polyurethane materials";

Column 16,  
Lines 28 and 29, delete "being oriented by contrast at an acute angle $A_{148d}$ to longitudinal axis $L_{38A}$ distal of attachment location 60";  
Line 32, after "sleeve 38A" insert -- being oriented by contrast at an acute angle $A_{148d}$ to longitudinal axis $L_{38A}$ distal of attachment location 60 --;  
Line 34, change "wing 150" to -- wing 140 --;  
Line 40, change "3 8B" to -- 38B --; and  
Line 64, change "3 8C" to -- 38C --.

UNITED STATES PATENT AND TRADEMARK OFFICE
CERTIFICATE OF CORRECTION

PATENT NO. : 6,332,874 B1
DATED : December 25, 2001
INVENTOR(S) : Kenneth A. Eliasen et al.

It is certified that error appears in the above-identified patent and that said Letters Patent is hereby corrected as shown below:

<u>Column 18,</u>
Line 19, change "implant able" to -- implantable --; and

<u>Column 19,</u>
Line 14, after "tube" insert -- at an attachment location thereon --.

Signed and Sealed this

Twenty-third Day of March, 2004

JON W. DUDAS
*Acting Director of the United States Patent and Trademark Office*